(12) United States Patent
Daunert et al.

(10) Patent No.: US 8,663,927 B2
(45) Date of Patent: Mar. 4, 2014

(54) SYSTEMS AND METHODS FOR DIAGNOSIS AND MONITORING OF BACTERIA-RELATED CONDITIONS

(75) Inventors: Sylvia Daunert, Lexington, KY (US); Sapna K. Deo, Fishers, IN (US); Patrizia Pasini, Lexington, KY (US); Anjali Kumari Struss, San Diego, CA (US); Harohalli Shashidhar, Lexington, KY (US); Deborah R. Auer Flomenhoft, Lexington, KY (US); Nilesh Raut, Lexington, KY (US)

(73) Assignee: University of Kentucky Research Foundation, Lexington, KY (US)

(*) Notice: Subject to any disclaimer, the term of this patent is extended or adjusted under 35 U.S.C. 154(b) by 650 days.

(21) Appl. No.: 12/676,287

(22) PCT Filed: Sep. 10, 2008

(86) PCT No.: PCT/US2008/075882
§ 371 (c)(1),
(2), (4) Date: Jun. 1, 2010

(87) PCT Pub. No.: WO2009/036081
PCT Pub. Date: Mar. 19, 2009

(65) Prior Publication Data
US 2010/0291566 A1  Nov. 18, 2010

Related U.S. Application Data

(60) Provisional application No. 60/971,228, filed on Sep. 10, 2007.

(51) Int. Cl.
*G01N 33/53* (2006.01)

(52) U.S. Cl.
USPC .............................. 435/6.16; 435/34; 435/7.1

(58) Field of Classification Search
None
See application file for complete search history.

(56) References Cited

U.S. PATENT DOCUMENTS

| 5,591,872 A | 1/1997 | Pearson et al. |
| 5,593,827 A * | 1/1997 | Bycroft et al. ............... 435/6.13 |
| 5,759,798 A * | 6/1998 | Dunlap .......................... 435/29 |

(Continued)

FOREIGN PATENT DOCUMENTS

| WO | WO9927786 | 6/1999 |
| WO | WO2004083385 | 9/2004 |

(Continued)

OTHER PUBLICATIONS

Favre-Bonte, Sabine et al, BMC Microbiology, vol. 7, Apr. 2007, numbered pp. 1-12, journal pp. 33-44, Autoinducer production and quorum-sensing dependent phenotypes of *Pseudomonas aerginosa* vary according to isolation site during colonization of intubated patients.*

(Continued)

*Primary Examiner* — Albert Navarro
*Assistant Examiner* — Ginny Portner
(74) *Attorney, Agent, or Firm* — Stites & Harbison PLLC; Mandy Wilson Decker

(57) ABSTRACT

The presently-disclosed subject matter provides systems, methods, and kits for diagnosing and/or monitoring a bacteria-related condition of interest in a subject by providing a cell sensing system, each system containing a reporter molecule capable of detecting binding of a quorum sensing molecule and capable of generating a detectable signal.

43 Claims, 14 Drawing Sheets

(56) References Cited

U.S. PATENT DOCUMENTS

| | | | |
|---|---|---|---|
| 6,544,729 B2* | 4/2003 | Sayler et al. | 435/5 |
| 6,559,176 B1 | 5/2003 | Bassler et al. | |
| 6,720,415 B2 | 4/2004 | Bassler et al. | |
| 6,780,890 B2 | 8/2004 | Bassler et al. | |
| 6,855,513 B1 | 2/2005 | Whiteley et al. | |
| 6,936,435 B2 | 8/2005 | Bassler et al. | |
| 6,942,986 B2* | 9/2005 | Bassler et al. | 435/7.32 |
| 6,958,219 B2 | 10/2005 | Kende et al. | |
| 7,020,560 B2* | 3/2006 | Sayler et al. | 702/19 |
| 7,326,542 B2* | 2/2008 | Bassler et al. | 435/32 |
| 7,365,184 B2* | 4/2008 | Jones et al. | 536/23.7 |
| 7,384,639 B2* | 6/2008 | Kende et al. | 424/197.11 |
| 7,651,843 B2* | 1/2010 | Stubbs et al. | 435/7.2 |
| 7,812,134 B2* | 10/2010 | Charlton et al. | 530/387.3 |
| 8,293,478 B2* | 10/2012 | Souno et al. | 435/6.15 |
| 2002/0072052 A1* | 6/2002 | Bassler et al. | 435/4 |
| 2002/0177715 A1 | 11/2002 | Pesci et al. | |
| 2003/0027241 A1* | 2/2003 | Sayler et al. | 435/29 |
| 2003/0095985 A1 | 5/2003 | Kende et al. | |
| 2003/0104606 A1 | 6/2003 | Bassler et al. | |
| 2003/0148414 A1* | 8/2003 | Bassler et al. | 435/32 |
| 2004/0033548 A1* | 2/2004 | Bassler et al. | 435/7.32 |
| 2004/0033549 A1 | 2/2004 | Greenberg et al. | |
| 2004/0097402 A1 | 5/2004 | Bassler et al. | |
| 2004/0147592 A1* | 7/2004 | Quay | 514/424 |
| 2004/0156856 A1 | 8/2004 | Kende et al. | |
| 2004/0180829 A1 | 9/2004 | Bassler et al. | |
| 2005/0074827 A1 | 4/2005 | Muh et al. | |
| 2005/0250841 A1 | 11/2005 | Pearson et al. | |
| 2006/0165704 A1* | 7/2006 | Charlton et al. | 424/164.1 |
| 2006/0198817 A1* | 9/2006 | Alverdy | 424/78.38 |
| 2007/0020660 A1 | 1/2007 | Burczynski et al. | |
| 2007/0072174 A1* | 3/2007 | Sayler et al. | 435/5 |
| 2007/0203128 A1 | 8/2007 | Ammendola et al. | |
| 2007/0298032 A1* | 12/2007 | Robinson et al. | 424/131.1 |
| 2009/0215079 A1* | 8/2009 | Ostermann et al. | 435/7.2 |
| 2010/0291566 A1 | 11/2010 | Daunert et al. | |
| 2010/0304379 A1 | 12/2010 | Daunert et al. | |
| 2011/0117661 A1 | 5/2011 | Daunert et al. | |
| 2011/0229415 A1 | 9/2011 | Daunert et al. | |

FOREIGN PATENT DOCUMENTS

| | | |
|---|---|---|
| WO | WO2005046713 | 5/2005 |
| WO | WO2006063133 | 6/2006 |
| WO | WO2007065423 | 6/2007 |
| WO | WO2009021026 | 2/2009 |
| WO | WO2009021039 | 2/2009 |
| WO | WO2009021052 | 2/2009 |
| WO | WO2009036070 | 3/2009 |
| WO | WO2009036081 | 3/2009 |

OTHER PUBLICATIONS deKievit, Teresa R et al, Infection and Immunity, 2000, vol. 68(9), pp. 4839-4849, Bacterial Quorum Sensing in Pathogenic Relationships.*

Erickson, David L et al, Infection and Immunity, vol. 70(4), pp. 1783-1790, *Pseudomonas aeruginosa* Quorum-Sensing Systems May control Virulence Factor expression in the Lungs of Patients with Cystic Fibrosis.*

Lu, Lingeng et al, Avian Diseases, vol. 49(1), pp. 74-80, 2005, Autoinducer 2-like activity in Poultry-Associated Enteric Bacteria in Response to Subtherapetuic Antibiotic Exposure.*

Kuo, A et al, Journal of Bacteriology, 1994, vol. 176(24), pp. 7558-7565, vol. 176(24) Multiple N-Acyl-L-Homoserine Lactone Autoinducers of Luminescence in the Marine Symbiotic Bacterium *Vibrio fisheri*.*

Seed, PC et al, Journal of Bacteriology, 1995, vol. 177(3), pp. 654-659, vol. 177(3), Activation of the *Pseudomonas aeruginosa* lasI Gene by LasR and the *Pseudomonas* Autoinduction Regulatory Hierarchy.*

Schaber, J Andy et al, Journal of Medical Microbiology, 2004, vol. 53, pp. 841-853, Analysis of quorum sensing-deficient clinical isolates of *Pseudomonas aeruginosa*.*

Bassler, B. L.; Wright, M.; Silverman, M. R. Mol. Microbiol. 1994, 13(2), 273-286.

Chacon, O.; Bermudez, L.E.; Barletta, R. G. Annu. Rev. Microbiol. 2004, 58. 329-363.

Chandran, et al., "Inflammatory bowel disease: dysfunction of GALT and gut bacterial flora (II)," Surgeon. Jun. 2003; 1(3):125-36.

Middleton, B.; Rodgers, H.C.; Camara, M.; Knox, A.J.; Williams, P.; Hardman, A. FEMS Microbiol. Lett. 2002, 207, 1-7.

Crama-Bohbouth, G.; Lems-van Kao, P.; Weterman, I.T.; Biermond, I.; Pena, A.S. Dig. Dis. Sci. 1984, 29, 1089-1092.

Daunert, S.; Barrett, G.; Feliciano, J. S.; Shetty, R. S.; Shrestha, S.; Smith-Spencer, W. Chem. Rev. 2000, 100, 2705-2738.

Dong, et al., "Quenching quorum-sensing-dependent bacterial infection by an N-acyl homoserine lactonase," Nature. Jun. 2001; 411(6839):813-7.

Eberl L., "N-acyl homoserine lactone-mediated gene regulation in gram-negative bacteria," Syst. Appl. Microbiol. Dec. 1999; 22(4):493-506.

Falcão, et al., "Cell-to-cell signaling in intestinal pathogens," Curr. Issues Intest. Microbiol. Mar. 2004; 5(1):9-17.

Feliciano, J.; Pasini, P.; Deo, S. K.; Daunert, S. In Photoproteins in Bioanalysis; Daunert, S., Deo, S. K., Eds.; Wiley-VCH: Weinheim, 2006; pp. 131-154.

Gu, M. B.; Mitchell, R. J.; Kim, B. C. Adv. Biochem. Eng. Biotechnol. 2004, 87, 269-305.

Hardman, et al., "Quorum sensing and the cell-cell communication dependent regulation of gene expression in pathogenic and non-pathogenic bacteria," Antonie Van Leeuwenhoek. Nov. 1998; 74(4):199-210.

Hentzer, M.; Givskov, M. J. Clin. Invest. 2003, 112, 1300-1307.

Jarvas, K. G.; Giron, J.A.; Jerse, A. E.; McDaniel, T.K.; Donnenberg, M. S.; Kaper, J.B. Proc. Natl. Acad. Sci. U. S. A. 1995, 92, 7996-8000.

Kaufman, E.; Lamster, I. B. Crit. Rev. Oral Biol. Med. 2002, 13, 197-212.

Kjelleberg, S.; Molin, S. Curr. Opin. Microbiol. 2002, 5, 254-258.

Kumari A, et al., "Biosensing systems for the detection of bacterial quorum signaling molecules," Anal. Chem. Nov. 2006; 78(22): 7603-9.

Miller, M.B.; Bassler, B.L. Annu. Rev. Microbiol. 2001, 55, 165-199.

Miller, S.T., et al. Molecular Cell. 2004, 15, 677-687.

Mok, K. C.; Wingreen, N. S.; Bassler, B. L. The EMBO J 2003, 22(4), 870-881.

Naylor, L. H. Biochem. Pharmacol. 1999, 58. 749-757.

Ripp S, et al., "Linking bacteriophage infection to quorum sensing signaling and bioluminescent bioreporter monitoring for direct detection of bacterial agents," Appl. Microbiol. Mar. 2006; 100(3):488-99.

Yates, E. A.; Philipp, B.; Buckley, C.; Atkinson, S.; Chhabra, S. R.; Sockett, R.E.; Goldner, M.; Dessaux, Y.; Camara, M.; Smith, H.; Williams, P. Infect. Immun. 2002, 70. 5635-5646.

Schaefer, A. L.; Hanzelka, B.L.; Eberhard, A.; Greenberg, E.P. J. Bacteriol. 1996, 178, 2897-2901.

Singh PK, et al., "Quorum-sensing signals indicate that cystic fibrosis lungs are infected with bacterial biofilms," Nature. Oct. 2000; 407(6805):762-4.

Smith, R. S.; Iglewski, B. H. J. Clin. Invest. 2003, 112, 1460-1465.

Steindler L, et al., "Detection of quorum-sensing N-acyl homoserine lactone signal molecules by bacterial biosensors," FEMS Microbiol. Lett. Jan. 2007; 266(1): 1-92.

Taga, M.E.; Bassler, B.L. Proc. Natl. Acad. Sci. U. S. A. 2003, 100 Suppl 2, 14549-14554.

Van Dyk, T. K.; Rosson, R. Methods Mol. Biol. 1998, 102, 85-95.

Winson, M. K.; Swift, S.; Fish, L.; Throup, J. P., Jorgensen, F.; Chhabra, S. R.; Bycroft, B.W.; Williams, P.; Stewart, G. S. FEMS Microbiol. Lett. 1998, 163, 185-192.

* cited by examiner

| | Structure | Microorganism |
|---|---|---|
| N-acyl-homoserine lactone (AHL) | 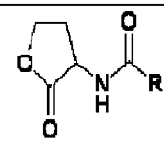 | |
| N-butyryl-homoserine lactone (C4-HSL) | 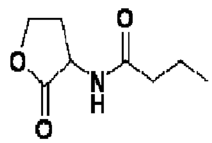 | *Pseudomonas aeruginosa* (RhlI) |
| N-hexanoyl-homoserine lactone (C6-HSL) | 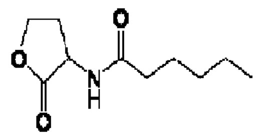 | *Chromobacterium violaceum* (CviI) |
| N-3-oxo-hexanoyl-homoserine lactone (3-oxo-C6-HSL) | 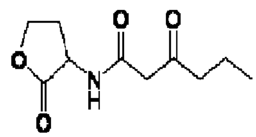 | *Vibrio fisheri* (LuxI) |
| N-octanoyl-homoserine lactone (C8-HSL) | 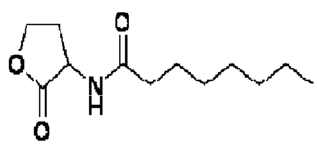 | *Burkholderia cepacia* (CepI) |
| N-3-oxo-octanoyl-homoserine lactone (3-oxo-C8-HSL) | 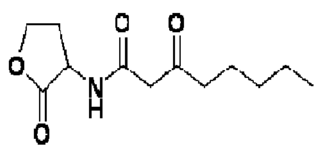 | *Agrobacterium tumefaciens* (TraI) |
| N-3-oxo-dodecanoyl-homoserine lactone (3-oxo-C12-HSL) | 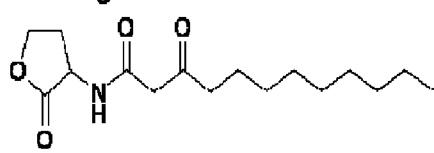 | *Pseudomonas aeruginosa* (LasI) |

FIGURE 1

SYSTEMS AND METHODS FOR DIAGNOSIS AND MONITORING OF BACTERIA-RELATED CONDITIONS

RELATED APPLICATIONS

This application claims priority from U.S. Provisional Application Ser. No. 60/971,228 filed Sep. 10, 2007, which is incorporated herein by this reference.

GOVERNMENT INTEREST

Subject matter described herein was made with U.S. Government support under Grant Number CHE-0416553 awarded by the National Science Foundation (NSF). The government has certain rights in the described subject matter.

TECHNICAL FIELD

The presently-disclosed subject matter relates to diagnosing and monitoring conditions of interest. In particular, the presently-disclosed subject matter relates to diagnosing and monitoring bacteria-related conditions.

INTRODUCTION AND GENERAL CONSIDERATIONS

Bacterial quorum sensing (QS) is a cell-to-cell communication phenomenon whereby bacterial cells produce signaling molecules intracellularly, which are released into the environment. Although these signaling molecules diffuse in and out of cells, the concentration of the signaling molecules in the environment reflects the population of bacteria that are present in a given environment or, in other words, the cell density of the bacterial population. To date, a variety of signaling molecules, termed quorum sensing molecules (QSM), have been identified, including N-acyl homoserine lactones (AHLs), which are used by many gram-negative bacteria; and oligopeptides, which are used by many gram-positive bacteria. In addition, a family of autoinducers, known as AI-2, has been identified and is produced by both gram-positive and gram-negative bacteria. [1] The quorum sensing process regulates the gene expression necessary for many bacterial activities including biofilm formation, light production, formation of virulence determinants, transfer of carcinogenic Ti plasmid, and several others. [1] The mechanism by which bacteria cause disease involves a delay in the expression of the genes responsible for the formation of virulence factors until the quorum sensing process produces a large enough bacterial population that it is capable of overwhelming the host defense system. [3]

Further, it is appreciated that once the concentration of the signaling molecules reaches a specific level, the bacteria can monitor population density and alter their group behavior. [3] In this regard, the QSMs bind to their sensor/regulatory protein, resulting in the activation of quorum sensing-dependent virulence/target genes.

Bacteria are thought to play an important role in many disorders ranging from infections to chronic inflammation. Among those, there are numerous reports in both animal models and humans that bacteria play a significant role in gastrointestinal (GI) diseases, such as inflammatory bowel disease (IBD). [4] Inflammatory bowel disease, which includes Crohn's disease (CD) and ulcerative colitis (UC), is a chronic gastrointestinal inflammatory condition with unknown etiology. To support the involvement of bacteria in these diseases are the identification of serologic markers against microbial antigens and the successful use of antibiotic therapy in subjects with Crohn's disease, as well as the observation that colitis cannot be induced in animals without bacterial flora. [5] Additionally, there is evidence for the involvement of quorum sensing in the pathogenesis of several diseases. For instance, bacteria-producing signaling molecules have been shown to be responsible for biofilm formation in the lungs. [6] These signaling molecules have been detected in the sputum of subjects with cystic fibrosis [7] and have been suspected to be involved in several illnesses of the GI Tract. [5,8,9] Interestingly, signaling molecules have been shown to induce several chemokines and cytokines responsible for inflammation, and inhibit others that are immunosuppressive in nature, in both in vitro and in vivo experiments. [10]

To date, there is a lack of quick and non- or minimally invasive methods for the monitoring of acute and chronic bacteria-related conditions. Crohn's disease, for example, usually occurs in the lower part of the small intestine, i.e., the ileum, but it can affect any part of the digestive tract, from the mouth to the anus. Crohn's disease exacerbation is usually diagnosed with a combination of clinical symptoms and blood tests for non-specific inflammatory markers, and in some instances an endoscopy. Methods and systems allowing for the non-invasive monitoring of subjects with Crohn's disease and other bacteria-related conditions would allow for early identification of exacerbations and, consequently, for therapy administration before the onset of a "flare-up," thereby decreasing the hardship that such conditions cause to the subjects. Accordingly, there remains a need in the art for systems and methods for diagnosing and monitoring bacteria-related conditions.

SUMMARY

The presently-disclosed subject matter meets some or all of the above-identified needs, as will become evident to those of ordinary skill in the art after a study of information provided in this document. This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter provides, in some embodiments, a method of diagnosing a bacteria-related condition in a subject. In some embodiments, the method comprises providing a biological sample from a subject; determining an amount in the sample of at least one quorum sensing molecule (QSM); and comparing the amount of the at least one QSM in the sample, if present, to a control level of the at least one QSM. If there is a measurable difference in the amount of the at least one QSM in the sample as compared to the control level, the subject can then be diagnosed as having the bacteria-related condition of interest or a risk thereof.

In some embodiments, the QSM is an N-acyl homoserine lactone (AHL) or an autoinducer-2 (AI-2). In some embodiments, the AHL is selected from: N-butyryl homoserine lactone (C4-HSL), N-hexanoyl homoserine lactone (C6-HSL), N-(3-oxo)-hexanoyl homoserine lactone (3-oxo-C6-HSL), N-octanoyl homoserine lactone (C8-HSL), N-(3-oxo)-octanoyl homoserine lactone (3-oxo-C8-HSL), N-decanoyl homoserine lactone (C10-HSL), N-dodecanoyl homoserine lactone (C12-HSL), N-(3-oxo)-dodecanoyl homoserine lactone (3-oxo-C12-HSL), N-tetradecanoyl homoserine lactone (C14-HSL), and combinations thereof.

In some embodiments, determining the amount in the sample of the at least one QSM comprises determining the amount in the sample of the at least one QSM using a cell sensing system. In some embodiments, the cell sensing system comprises a bacterial cell; a regulatory protein within the bacterial cell for binding at least one QSM; and, a reporter molecule within the bacterial cell for detecting binding of the QSM to the regulatory protein, where the reporter molecule generates a detectable signal upon binding of the QSM to the regulatory protein. In some embodiments, the cell sensing system further comprises a substrate supporting the bacterial cell and a signal reader for detecting the signal generated by the reporter molecule. In some embodiments, the bacterial cell comprises a heterologous reporter gene cassette that comprises a promoter operatively linked to a nucleotide sequence encoding the reporter molecule. In some embodiments, the reporter gene cassette is luxCDABE. In some embodiments, the reporter gene cassette is luxCDABE, the promoter is $P_{rhlI}$, and the regulatory peptide is RhlR. In some embodiments, the reporter gene cassette is luxCDABE, and the promoter and regulatory peptide are $P_{lasI}$ and LasR, respectively.

Further, in some embodiments of the presently-disclosed subject matter, the QSM-regulatory complex has binding affinity for the promoter such that the regulatory peptide binds the promoter and activates expression of the reporter molecule to thereby generate a detectable signal. In some embodiments, the detectable signal is bioluminescence. In some embodiments, an amount of the detectable signal correlates to a concentration of the QSM.

Still further provided, in some embodiments of the presently-disclosed methods, the determined amount of the at least one QSM can be used to select or modify a treatment for the bacteria-related condition of interest. In some embodiments, a method for determining whether to initiate or continue prophylaxis or treatment of a bacteria-related condition of interest in a subject is provided. In some embodiments, the method comprises providing a series of biological samples over a time period from the subject; analyzing the series of biological samples to determine an amount in each of the biological samples of the at least one QSM; and, comparing any measurable change in the amounts of the at least one QSM in each of the biological samples to thereby determine whether to initiate or continue the prophylaxis or treatment of the bacteria-related condition of interest.

In some embodiments of the methods of the presently-disclosed subject matter, the subject is human. In some embodiments, a biological sample is provided from the subject. In some embodiments, the biological sample is a saliva sample, and, in some embodiments, the biological sample, is a stool sample.

In some embodiments, the bacteria-related condition is a bacterial infection. In some embodiments, the bacteria-related condition is an inflammation, such as, in some embodiments, a chronic inflammation. In some embodiments, the bacteria-related condition of interest is a condition of the gastro-intestinal tract. In some embodiments, the condition is an inflammatory bowel disease (IBD), including, in some embodiments, Crohn's disease and ulcerative colitis.

Still further provided, in some embodiments of the presently-disclosed subject matter, is a kit for diagnosing a bacteria-related condition of interest in a subject. In some embodiments, the kit comprises a cell sensing system in accordance with the presently-disclosed subject matter and instructions for using the kit.

Accordingly, it is an object of the presently-disclosed subject matter to provide systems, methods, and kits for diagnosing and monitoring a bacteria-related condition of interest in a subject. This object is achieved in whole or in part by the presently-disclosed subject matter.

An object of the presently-disclosed subject matter having been stated hereinabove, and which is achieved in whole or in part by the presently-disclosed subject matter, other objects and advantages will become evident to those of ordinary skill in the art after a study of the following description of the presently-disclosed subject matter, Figures, and non-limiting Examples.

BRIEF DESCRIPTION OF THE DRAWINGS

FIG. 1 includes the chemical structures of N-acyl homoserine lactones (AHLs) produced by different bacterial species, and the respective LuxI homologues responsible for AHL synthesis in each bacterial species.

DESCRIPTION OF EXEMPLARY EMBODIMENTS

Figure 2A:
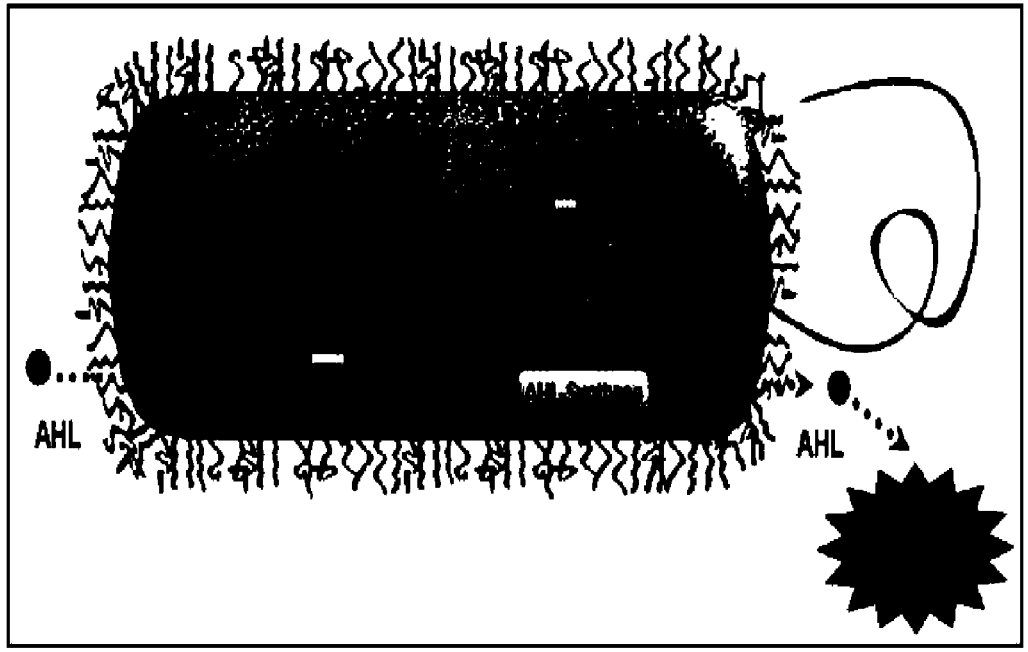
FIG. 2 contains a schematic representation of AHL-dependent regulation of quorum sensing in LuxR/LuxI-type systems (FIG. 2A) and a schematic representation of the plasmids pSB1075 and pSB406, which contain lasR and rhlR regulatory genes, respectively, fused with the reporter gene cassette luxCDABE.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the following terms are believed to be well understood by one of ordinary skill in the art, the following definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Bacteria communicate with neighboring bacterial cells by producing signaling molecules intracellularly that are released into the environment, and the concentration of these signaling molecules reflects the cell density of the bacterial population. Once the concentration of the signaling molecules reaches a specific level, the bacteria can monitor their population density and alter their group behavior, including, but not limited to, altering and controlling the expression of certain specialized genes depending on the size of the bacterial population. This phenomenon is termed "quorum sensing" and is a process whereby the expression of genes necessary for many bacterial activities, such as biofilm formation, light production, formation of virulence factors, and others, is regulated. For example, the mechanism by which bacteria cause disease involves a delay in the expression of genes responsible for formation of virulence factors until the quorum sensing process produces a sufficiently large bacterial population that is capable of overwhelming a host's defense system.

The signaling molecules that are involved in the process of quorum sensing are referred to herein as "quorum sensing molecules" (QSM). Many gram-negative bacteria use N-acyl homoserine lactones as their QSMs, while many gram-positive bacteria employ oligopeptides. Additionally, a family of autoinducers, known as autoinducer-2 (AI-2), can function as QSMs and are produced by both gram-positive and gram-negative bacteria.

Given the role of the QS process and QSMs in bacterial cell-to-cell communication, as well as the role of this phenomenon in the pathogenesis of many bacteria-related conditions, information about the timing and level of expression of QSMs in bacteria-related conditions is desirable to obtain. Systems and methods capable of identifying the presence of and quantitating QSMs in a particular bacteria-related condition of interest can provide information useful for understanding how each bacteria-related condition evolves and is maintained. Such understanding can prove useful in the diagnosis and characterization of a number of bacteria-related conditions and can allow these conditions to be diagnosed and/or monitored such that a treatment can be selected or modified depending on the amount of QSMs in a biological sample from a subject.

The presently-disclosed subject matter includes systems, methods, and kits for diagnosing and/or monitoring a bacteria-related condition of interest in a subject. The term "bacteria-related condition" is used herein to refer to conditions whose symptoms are caused directly or indirectly by the invasion and/or colonization of bacteria. For example, in some embodiments of the presently-disclosed subject matter, the bacteria-related condition can be a bacterial infection, an acute or chronic inflammation, a condition of the gastrointestinal tract, or an inflammatory bowel disease (IBD), such as Crohn's disease (CD) or ulcerative colitis (UC).

In some embodiments, a method of detecting and/or monitoring a bacteria-related condition is provided, which can lead to diagnosis of the condition. In some embodiments, the method includes: providing a biological sample from the subject; determining an amount in the sample of at least one QSM; comparing the amount of the at least one QSM in the sample, if present, to a control level of the at least one QSM, wherein the subject is diagnosed as having the bacteria-related condition of interest or a risk thereof if there is a measurable difference in the amount of the at least one QSM in the sample as compared to the control level.

The term "biological sample" as used herein refers to a sample capable of comprising a QSM, which is derived from a subject. The biological sample can be utilized for the detection of the presence and/or level of a QSM of interest in the sample. Exemplary biological fluids include, but are not limited to, saliva, stool, sputum, blood, plasma, serum, and urine.

In some embodiments, the biological sample comprises saliva. In some embodiments, the sample comprises stool.

In some embodiments, the QSM is selected from the groups consisting of: N-acyl homoserine lactone (AHL) and autoinducer-2 (AI-2). It is appreciated that the family of QSMs known as AI-2 includes a number of QSMs that interconvert into each other and are capable of existing in equilibrium in solution. [22] Further, many different types of AHLs have been reported in the literature. In some embodiments of the presently-disclosed subject matter, the AHL is selected from: N-butyryl homoserine lactone (C4-HSL), N-hexanoyl homoserine lactone (C6-HSL), N-(3-oxo)-hexanoyl homoserine lactone (3-oxo-C6-HSL), N-octanoyl homoserine lactone (C8-HSL), N-(3-oxo)-octanoyl homoserine lactone (3-oxo-C8-HSL), N-decanoyl homoserine lactone (C10-HSL), N-dodecanoyl homoserine lactone (C12-HSL), N-(3-oxo)-dodecanoyl homoserine lactone (3-oxo-C12-HSL), N-tetradecanoyl homoserine lactone (C14-HSL), and combinations thereof.

The terms "diagnosing" and "diagnosis" as used herein refer to methods by which the skilled artisan can estimate and even determine whether or not a subject is suffering from a given bacteria-related condition. The skilled artisan often makes a diagnosis on the basis of one or more diagnostic indicators. The presently-disclosed subject matter provides for the measurement of one or more QSMs as diagnostic indicators, the amount (including presence or absence) of which is indicative of the presence, severity, or absence of a bacteria-related condition.

Along with diagnosis, clinical prognosis is also an area of great concern and interest. It is important to know the aggressiveness of particular bacteria-related conditions and the likelihood of remissions and/or exacerbations in order to plan the most effective therapy. Crohn's disease, for example, is managed by several alternative strategies. In some cases, antibiotic therapy may be successfully utilized, while, in other cases, anti-inflammatory, steroid, or antibody therapies, or combinations thereof, are employed. If a more accurate prognosis can be made, appropriate therapy, and in some instances less severe therapy for the subject can be chosen. Measurement of one or more QSMs can be useful in order to separate subjects with good prognosis, who will need no further therapy, from those more likely to have recurring symptoms or exacerbations, who might benefit from more intensive treatments.

As such, "making a diagnosis" or "diagnosing", as used herein, is further inclusive of making a prognosis, which can provide for predicting a clinical outcome (with or without medical treatment), selecting an appropriate treatment (or whether treatment would be effective), or monitoring a current treatment and potentially changing the treatment, based on the measure of QSMs present in a sample. As such, in some embodiments, a method of diagnosing a bacteria-related condition is provided that further comprises selecting or modifying a treatment for the bacteria-related condition that is based on the determined amount of the at least one QSM. Further, in some embodiments of the presently-disclosed subject matter, multiple determinations of the amounts of QSMs over time can be made to facilitate diagnosis and/or prognosis. A temporal change in the amount of QSMs can be used to predict a clinical outcome, monitor the progression of the bacteria-related condition and/or efficacy of appropriate therapies directed against the bacteria-related condition of interest. In such an embodiment, for example, one might expect to see a decrease in the amount of QSMs in a biological sample over time during the course of effective therapy.

The presently-disclosed subject matter further provides, in some embodiments, a method for determining whether to initiate or continue prophylaxis or treatment of a bacteria-related condition of interest in a subject. In some embodiments, the method comprises providing a series of biological samples over a time period from the subject; analyzing the series of biological samples to determine an amount of at least one QSM in each of the biological samples; and comparing any measurable change in the amounts of the at least one QSM in each of the biological samples. Any changes in the amounts of the at least one QSM over the time period can be used to predict clinical outcome, determine whether to initiate or continue the prophylaxis or therapy of the bacteria-related condition, and whether a current therapy is effectively treating the bacteria-related condition. For example, a first time point can be selected prior to initiation of a treatment and a second time point can be selected at some time after initiation of the treatment. QSM levels can be measured in each of the samples taken from different time points and qualitative and/or quantitative differences noted. A change in the amounts of the QSM levels from the first and second samples can be correlated with prognosis, determining treatment efficacy, and/or progression of the disease in the subject.

The terms "correlated" and "correlating," as used herein in reference to the use of diagnostic and/or prognostic biomarkers, such as QSMs, refers to comparing the presence or quantity of the QSM in a subject to its presence or quantity in subjects known to suffer from, or known to be at risk of, a given condition (e.g., Crohn's disease); or in subjects known to be free of a given condition, i.e. "normal subjects" or "control subjects". For example, a level of a QSM in a biological sample can be compared to a QSM level determined to be associated with a specific type of bacteria-related condition. The sample's QSM level is said to have been correlated with a diagnosis; that is, the skilled artisan can use the QSM level to determine whether the subject suffers from a specific type of bacteria-related condition, and respond accordingly. Alternatively, the sample's QSM level can be compared to a control QSM level known to be associated with a good outcome (e.g., the absence of a bacteria-related condition), such as an average level found in a population of normal subjects.

In certain embodiments, a diagnostic or prognostic biomarker is correlated to a condition or disease by merely its presence or absence. In other embodiments, a threshold level of a diagnostic or prognostic biomarker can be established, and the level of the indicator in a subject sample can simply be compared to the threshold level.

As noted, in some embodiments, multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of bacteria-related condition, or a given prognosis. Likewise, a decrease in the marker from the initial time to the second time can be indicative of a particular type or severity of bacteria-related condition, or a given prognosis. Furthermore, the degree of change of one or more markers can be related to the severity of the bacteria-related condition and future adverse events.

The phrase "determining an amount," and grammatical variations thereof, when used herein in reference to a QSM, refers to a qualitative (e.g., present or not present in the measured sample), quantitative (e.g., how much is present), or both, measurement of a QSM. The "control level" is an amount (including the qualitative presence or absence) or range of amounts of a QSM found in a comparable biological sample in subjects free of a bacteria-related condition, or at least free of the bacteria-related condition of interest being tested. As one non-limiting example of calculating the control level, the amount of a QSM present in a normal biological sample (e.g., blood, serum, plasma, urine, sputum, saliva, pleural fluid, peritoneal fluid, or cerebral spinal fluid) can be calculated and extrapolated for whole subjects.

In certain embodiments of the presently disclosed subject matter, determining the amount in the sample of the at least one QSM comprises determining the amount in the sample of the at least one QSM using a cell sensing system. The cell sensing system can include, in some embodiments, a bacteria cell, e.g., *Escherichia coli*; a regulatory protein within the bacterial cell for binding the at least one QSM; and a reporter molecule within the bacterial cell for detecting binding of the QSM to the regulatory protein, wherein the reporter molecule generates a detectable signal upon binding of the QSM to the regulatory peptide.

The phrase "cell sensing system" is used herein to refer to genetically engineered whole-cell biosensors, where genetic constructs are employed, and in which a regulatory peptide capable of recognizing a molecule of interest, such as a QSM, controls the expression of a reporter molecule. For example, when the target analyte, e.g. a QSM, is present in a sample, the regulatory protein recognizes the target analyte and activates transcription of the reporter molecule to generate a detectable signal. As such, when the transcription of the reporter molecule is induced in the presence of a target analyte, the reporter gene is expressed in a dose-dependent fashion and, consequently, the concentration of the inducing, target analyte can be determined by measuring the detectable signal that is generated by the reporter molecule.

In some embodiments, the regulatory protein of the cell sensing system is RhlR or a fragment thereof, or LasR or a fragment thereof The terms "protein," "polypeptide," and "peptide," which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The term "fragment" refers to a sequence that comprises a subset of another sequence. When used in the context of a nucleic acid or amino acid sequence, the terms "fragment" and "subsequence" are used interchangeably. A fragment of a nucleic acid sequence can be any number of nucleotides that is less than that found in another nucleic acid sequence, and thus includes, but is not limited to, the sequences of an exon or intron, a promoter, an enhancer, an origin of replication, a 5' or 3' untranslated region, a coding region, and a polypeptide binding domain. It is understood that a fragment or subsequence can also comprise less than the entirety of a nucleic acid sequence, for example, a portion of an exon or intron, promoter, enhancer, etc. Similarly, a fragment or subsequence of an amino acid sequence can be any number of residues that is less than that found in a naturally occurring polypeptide, and thus includes, but is not limited to, domains, features, repeats, etc. Also, similarly, it is understood that a fragment or subsequence of an amino acid sequence need not comprise the entirety of the amino acid sequence of the domain, feature, repeat, etc.

A fragment can also be a "functional fragment," in which the fragment retains a specific biological function of the nucleic acid sequence or amino acid sequence of interest. For example, a functional fragment of a regulatory peptide can include, but is not limited to, a DNA binding domain and an analyte binding domain.

Further, a bacterial cell of the presently-disclosed subject matter can be, for example, a transformed bacterial cell. The terms "transformed", "transgenic", and "recombinant" refer to a cell, such as a bacterial cell, into which a heterologous nucleic acid molecule has been introduced. The nucleic acid molecule can be stably integrated into the genome of the cell, and/or the nucleic acid molecule can be present as an extrachromosomal molecule (e.g., a plasmid). Such an extrachromosomal molecule can be auto-replicating. Transformed cells are understood to encompass not only the end product of a transformation process, but also transgenic progeny thereof. A "non-transformed," "non-transgenic", or "non-recombinant" host refers to a wild type organism, e.g., a cell, which does not contain the heterologous nucleic acid molecule. For example, in some embodiments, the bacterial cell has been transformed with a plasmid, such as a pSB406 or a pSB1075 plasmid, comprising a heterologous polynucleotide reporter gene cassette comprising a promoter operatively linked to a gene encoding the reporter molecule.

The term "reporter gene cassette" refers to a nucleic acid molecule capable of directing expression of a particular nucleotide sequence in an appropriate host cell, comprising a promoter and/or other regulatory sequences operatively linked to the nucleotide sequence of interest which can be operatively linked to termination signals. It also typically comprises sequences required for proper translation of the nucleotide sequence. The coding region usually encodes a polypeptide of interest but can also encode a functional RNA of interest. The reporter gene cassette comprising the nucleotide sequence of interest can be chimeric, meaning that at least one of its components is heterologous with respect to at least one of its other components. The reporter gene cassette can also be one that is naturally occurring but has been obtained in a recombinant form useful for heterologous expression.

Typically, however, the reporter gene cassette is heterologous with respect to the host; i.e., the particular DNA sequence of the reporter gene cassette does not occur naturally in the host cell and was introduced into the host cell or an ancestor of the host cell by a transformation event. The expression of the nucleotide sequence in the reporter gene cassette can be under the control of a constitutive promoter or of an inducible promoter that initiates transcription only when the host cell is exposed to some particular external stimulus.

The term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The terms "heterologous", "recombinant", and "exogenous", when used herein to refer to a nucleic acid sequence (e.g. a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA segments can be expressed to yield exogenous polypeptides. In contrast, a "homologous" nucleic acid (or amino acid) sequence is a nucleic acid (or amino acid) sequence naturally associated with a host cell into which it is introduced.

The terms "associated with", "operably linked", and "operatively linked" refer to two nucleic acid sequences that are related physically or functionally. For example, a promoter or regulatory DNA sequence is said to be "operatively linked with" a DNA sequence that encodes an RNA or a polypeptide if the two sequences are operatively linked, or situated such that the regulator DNA sequence will affect the expression level of the coding or structural DNA sequence.

In some embodiments of the presently-disclosed subject matter, an exemplary cell sensing system further comprises a substrate supporting the bacterial cell, and a signal reader for detecting the signal generated by the reporter molecule. In some embodiments, for example, the substrate can be a microfluidic platform, a container (e.g., a test tube or a well of a microtiter plate), an optic fiber, or a paper strip.

Figure 9A:
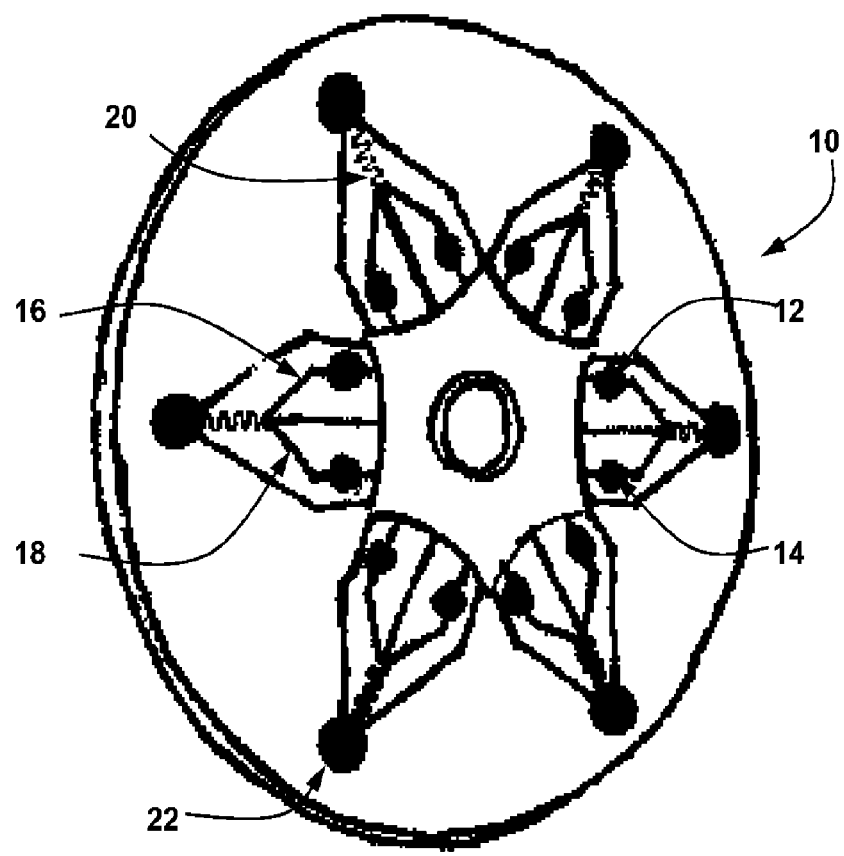
FIG. 9 includes a diagram of a microcentrifuge compact disc (CD) microfluidics platform (FIG. 9A) and a diagram of a microfluidics structure (FIG. 9B) of the CD microfluidics platform containing small wells for the addition of sensing bacterial cells and samples, and a detection chamber linked to the wells by a mixing channel.
Figure 9B:
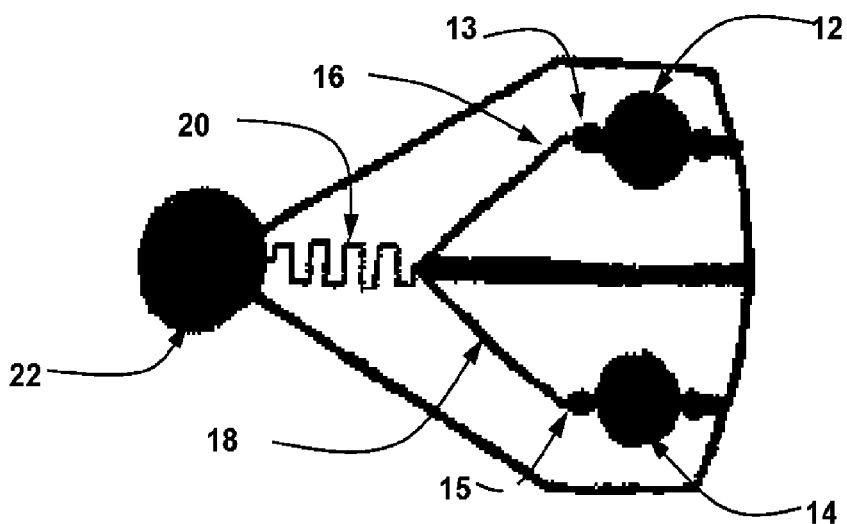

As one exemplary embodiment of a microfluidic platform using a sensing bacterial cell described herein, the presently-disclosed subject matter provides an effective packaging method for the storage, transport, and use of sensing bacterial cells adapted to a microcentrifugal microfluidics platform. The microfluidic platform can comprise a structure of low microliter to nanoliter-volume reservoirs connected by micrometer-dimension channels manufactured, for example, by computer numerical control (CNC) machining. An exemplary embodiment of a microfluidic platform 10 is shown in FIG. 9A. In some embodiments, the platform 10 comprises a poly(methyl methacrylate) (PMMA) substrate and has a disk-shape similar to that of a compact disk (CD). With reference to FIG. 9B, the force used for pumping solutions from reservoirs 12 and 14 through reservoir channels 16 and 18 in flow communication with reservoirs 12 and 14, respectively, is a centrifugal force exerted on the fluids when the disk platform 10 is spun on a rotor. The rpm at which a solution will flow from a given reservoir 12 or 14 into a reservoir channel 16 or 18 can be controlled by the size of a burst valve 13 or 15 positioned at the juncture of the reservoirs 12 and 14 and the reservoir channels 16 and 18. Surface tension and fluid/substrate interactions can effectively trap a flowing fluid where a reservoir 12 or 14 meets a burst valve 13 or 15 until these forces are overcome by sufficient centrifugal force.

The reservoirs 12 and 14 can be sealed and one can comprise the presently-disclosed sensing bacteria cells suspended in a liquid formulation, while the other reservoir can comprise a sample of interest, e.g. a saliva or stool sample known to or suspected of containing a QSM. The suspension or samples can be added in advance and sealed in the reservoirs 12 and 14, or added just prior to addition of centrifugal force. When the microfluidic platform 10 is spun, the sensing bacterial cells and the sample of interest are forced from the reservoir 12 or 14, through the reservoir channels 16 or 18, and into a mixing channel 20 where fluids from each of reservoirs 12 and 14 are mixed with each other, and if desired, other reagents. The sensing bacterial cells and sample of interest are thus mixed together and pool in a detection chamber 22, wherein a detectable signal is then generated if there is an amount in the sample of at least one QSM.

In one particular embodiment, for example, an aliquot (e.g., 15-25 µL) of the sensing bacterial cells are placed in a first reservoir (e.g., reservoir 12) and an aliquot (e.g., 15-25 µL) of a sample of interest is placed in a second reservoir (e.g., reservoir 14). Upon spinning the CD microfluidic platform 10, the sensing bacterial cells and sample of interest are released from the two different reservoirs 12 and 14, respectively, pass through reservoir channels 16 and 18, respectively, mix passing through mixing channel 20, and pass into detection chamber 22. Expression of a reporter molecule by the sensing bacterial cells is then indicative of the presence of a QSM in the sample of interest, which can be measured by a signal reader, such as a photomultiplier tube (PMT). Thus, the entire assay can be performed directly on the microfluidics platform 10. The presently-disclosed platform is readily adaptable and provides for on-site testing not only in bedside and physician's office monitoring, but also in home-based disease management.

As discussed hereinabove, in some embodiments of the methods and systems making use of a cell sensing system, the transformed bacterial cell can include a heterologous reporter gene cassette comprising a promoter operatively linked to a nucleotide sequence encoding the reporter molecule. In some embodiments, the QSM-regulatory protein complex can have a binding affinity for the promoter, such that the regulatory peptide binds the promoter and activates expression of the reporter molecule, thereby generating a detectable signal.

Reporter molecules capable of generating a detectable signal are known to those of ordinary skill in the art and include, but are not limited to, reporter molecules such as green fluorescent protein (GFP), β-galactosidase, and luciferase. Further, it is appreciated that genes encoding various reporter molecules can be inserted into a reporter gene cassette and used to monitor induction of an operon, depending on the desired detection system.

In some embodiments of the presently-disclosed subject matter, the reporter gene cassette is luxCDABE. In some embodiments, the reporter gene cassette is luxCDABE, the promoter is $P_{rhlI}$, and the regulatory peptide is RhlR. In some embodiments, the reporter gene cassette is luxCDABE, the promoter is $P_{lasI}$, and the regulatory peptide is LasR. The genes luxA and luxB in the luxCDABE reporter gene cassette encode bacterial luciferase, which, upon expression, can generate a bioluminescent signal upon reacting with its substrate, luciferin, and offers a low detection limit of approximately $10^{-18}$ mol. In this regard, it is noted that the genes luxC, luxD, and luxE of the reporter gene cassette encode the enzymes required for the synthesis and recycling of the bioluminescent substrate, and thus the cell sensing systems of the presently-disclosed subject matter offer the advantage of not requiring the external addition a substrate. In some embodiments, the detectable signal is bioluminescence. Further, in some embodiments, the intensity of the detectable signal can be quantitative, and it can be correlated to a concentration of the QSM.

The presently-disclosed subject matter further provides, in some embodiments, a kit for diagnosing a bacteria-related condition of interest in a subject. In some embodiments, the kit comprises a cell sensing system in accordance with the presently-disclosed subject matter and instructions for using the kit.

Further, with regard to the methods, systems, and kits of the presently-disclosed subject matter, the term "subject" includes both human and animal subjects. Thus, veterinary therapeutic uses are provided in accordance with the presently disclosed subject matter. As such, the presently-disclosed subject matter provides for the treatment of mammals such as humans, as well as animals of importance to humans The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Polynucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Materials and Methods for Examples 1-8

Materials

Vitamin-free casamino acids needed for preparing AB media, and Luria Bertani (LB) agar and broth were obtained from Difco (Sparks, Md.). Ampicillin and all N-acyl homoserine lactone (AHL) standard compounds were obtained from Sigma (St. Louis, Mo.). The chemical structures of exemplary AHLs tested are provided in FIG. 1. Autoinducer-2 (AI-2) was obtained from Omm Scientific (Dallas, Tex.). Acetonitrile was of high performance liquid chromatography (HPLC) grade and was from Fisher Scientific (Pittsburgh, Pa.). Distilled deionized water (Milli-Q Water Purification system, Millipore, Bedford, Mass.) was used for all the experiments. The 96-well microtiter plates were purchased from Costar (Corning, N.Y.).

The microcentrifuge utilized was from Eppendorf (Westbury, N.Y.). The orbital shaker incubator utilized was from Fisher Scientific (Fair Lawn, N.J.). Bioluminescent measurements were made using the FLUOSTAR OPTIMA™ microplate reader (BMG Labtech, Durham, N.C.).

Plasmids, Bacterial Strains, and Culture Conditions for AHL Sensing Systems

The bacterial strain *Escherichia coli* JM109 was purchased from Stratagene (Cedar Creek, Tex.). Plasmids pSB406 and pSB1075 were transformed respectively into competent *E. coli* JM109 cells using the standard protocol provided by the manufacturer. The transformed cells were grown at 37° C. overnight on LB agar plates containing 50 μg/mL ampicillin. Cells from a single colony were grown overnight at 37° C., 250 rpm in LB broth containing the same amount (w/v) of ampicillin. Glycerol stocks were prepared from those cell cultures and stored at −80° C. Fresh cell cultures were obtained from the glycerol stocks and grown in an orbital shaker at 37° C., 250 rpm until an optical density at 600 nm ($OD_{600\,nm}$) of 0.45-0.50 was reached.

Plasmids, Bacterial Strains, and Culture Conditions for AI-2 Sensing Systems

AB media used to grow *V. harveyi* strain BB170, a genetically modified strain that produces light in response to AI-2, was prepared as described previously. [23] The BB170 sensor strain was grown overnight in AB medium at 30° C. and 175 rpm. The following day, overnight grown BB170 culture was diluted in AB medium to obtain a final $O.D._{600\,nm}$ of 0.010.

Sample Collection and Preparation for the Detection of AHLs

Saliva and stool samples were employed for the detection of AHLs. The saliva samples were obtained from diseased and healthy (control) subjects. The stool samples were also obtained from diseased and healthy (control) subjects, and included samples from infants in the Newborn Intensive Care Unit (NICU) situated at the University of Kentucky (Lexington, Ky.). The saliva samples were collected in the mornings after brushing the teeth to minimize bulk collection of debris and the presence of oral bacteria. The samples were then processed by centrifuging them in sterile Eppendorf tubes at 13000 rpm for 2-3 min at room temperature. Supernatants were stored at −80° C. until analyzed. The stool samples were prepared by suspending and diluting the collected samples in distilled, deionized water. The final working dilution employed for stool samples was 1:1600 (w/v) in distilled, deionized water.

Sample Collection and Preparation for the Detection of AI-2

Human saliva samples used for the detection of AI-2 were also collected in the morning after brushing the teeth to minimize debris and oral bacteria. Any visible debris was removed by centrifuging the samples for up to 20 minutes at 14000 rpm at room temperature. The samples were then stored at −80° C. until needed.

Dose-Response Curves for AHLs

Commercially available AHLs were dissolved in acetonitrile to obtain $1 \times 10^{-2}$ M stock solutions, which were serially diluted with distilled, deionized water. AHL standard solutions of concentrations ranging from $1 \times 10^{-4}$ to $1 \times 10^{-9}$ M were obtained. A 1% solution of acetonitrile in distilled, deionized water was used as blank. The highest percent amount of acetonitrile used, i.e., 1% in water, did not prove to be toxic for the sensing cells. A total of 100 μL of each of these solutions was added in triplicate to culture tubes containing 1 mL of cell culture grown to an $OD_{600\,nm}$ of 0.45-0.50. These culture tubes were then incubated in an orbital shaker at 37° C. at 250 rpm for 2 h. The induced bioluminescence was then measured using a microplate reader after transferring 200 μL aliquots in triplicate from each culture tube into a 96-well micro titer plate. The total measuring time/well was 0.20 s. The light intensity was expressed in relative light units (RLU). The results were plotted using the software GraphPad Prism 4 (GraphPad Software, Inc., San Diego, Calif.).

Dose-Response Curves for AHLs in Sample Matrix

Dose-response curves were obtained in the sample matrix for both types of samples employed and described herein in the Examples, i.e., saliva and stool. Saliva samples from four healthy subjects were collected and then centrifuged. Equal volumes of the supernatants were mixed to obtain a pooled saliva sample. Acetonitrile $1 \times 10^{-2}$ M stock solutions of AHL compounds, e.g., C6-HSL and C14-HSL for the pSB406 and pSB1075 sensing systems, respectively, were serially diluted with the pooled saliva to obtain solutions of concentration ranging from $1 \times 10^{-4}$ to $1 \times 10^{-9}$ M. A 1% acetonitrile solution in pooled saliva was used as blank. A total of 100 μL of each of these solutions was added in triplicate to culture tubes containing 1 mL of cell culture, and the assay was performed as described hereinabove. A dose-response curve without matrix was also obtained as a reference in the same analytical run.

Stool samples from infants admitted to the NICU were collected and mixed in equal amounts to obtain a pooled stool sample. This was suspended and diluted 1:800 (w/v) in distilled, deionized water. Acetonitrile $1 \times 10^{-2}$ M stock solutions of C6-HSL and C14-HSL were serially diluted in distilled, deionized water to obtain standard solutions with concentrations ranging from $2 \times 10^{-4}$ to $2 \times 10^{-9}$ M. Equal volumes of these standard solutions and the 1:800 (w/v) pooled stool suspension were mixed to obtain AHL final concentrations ranging from $1 \times 10^{-4}$ to $1 \times 10^{-9}$ M in a 1:1600 (w/v) stool suspension. A 1% acetonitrile solution in 1:1600 (w/v) pooled stool suspension was used as blank. A total of 100 μL of each of these solutions was added in triplicate to culture tubes containing 1 mL of cell culture, and the assay was performed as described above. A dose-response curve without matrix was also obtained as a reference in the same analytical run.

Selection of Optimum Temperature for Sample Storage

Temperature stability studies of AHLs in saliva and stool samples were performed. Saliva samples were collected and divided into four aliquots of 450 μL each, before processing them. Three of these aliquots were kept at room temperature, 4° C., and −20° C., respectively, for 1 day and then centrifuged as described above. Supernatants were stored at −80° C. until analyzed. The fourth 450 μL aliquot was processed the same day it was collected, and the supernatant was kept at −80° C. until analyzed. Similarly, stool samples were collected and divided in aliquots that were stored at 4, −20, and −80° C. for up to 3 days. Aliquots of the same samples were processed and analyzed on the same day they were collected.

Analysis of Samples for AHLs

Saliva and stool samples were collected and processed as described hereinabove. A total of 100 μL of each of the processed biological samples, either saliva or stool, was added in triplicate to culture tubes containing 1 mL of cell culture, and the assay was performed as described above. Calibration curves using standard AHLs for both sensing systems were obtained in each analytical run.

Analysis of Samples for AI-2

Figure 14:
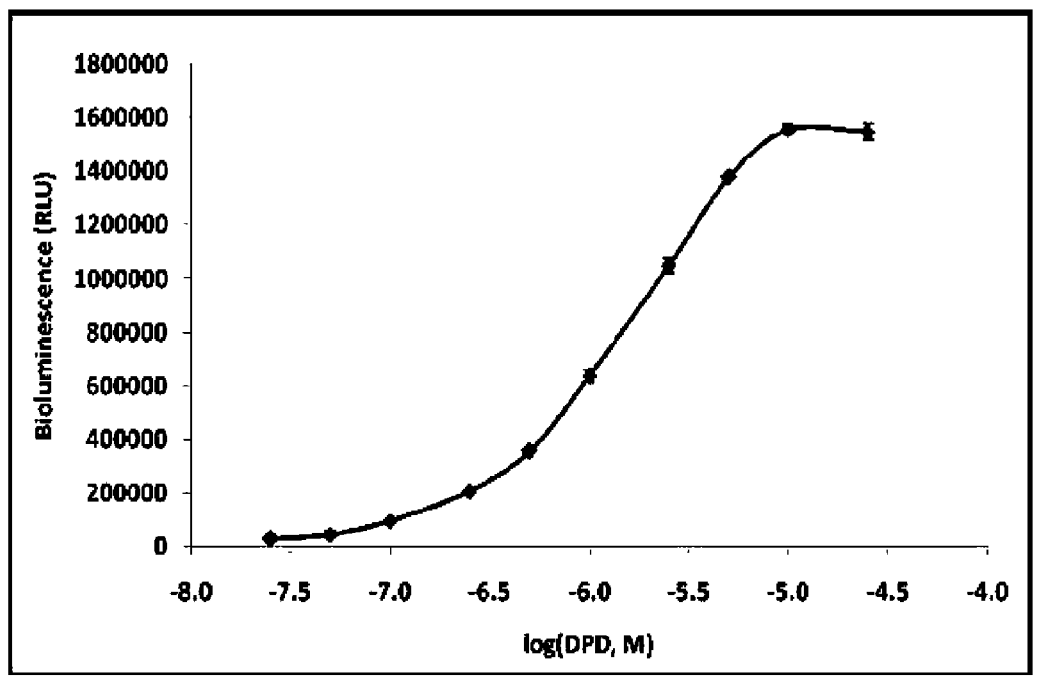
FIG. 14 is a calibration curve obtained using various concentrations of autoinducer-2 (AI-2).

Saliva samples were collected and processed as described hereinabove. The available stock of AI-2 was 3.9 mM. AI-2 standard solutions with concentrations ranging from $2.5 \times 10^{-4}$ M to $10^{-7}$ M were then prepared by using distilled, deionized water. 10 μL of AI-2 standard solution was incubated with 90 μL of BB170 bacterial culture at $O.D._{600\ nm}$ 0.010, in triplicate on a microtitre plate. 10 μL water incubated with 90 μL of BB170 served as a blank. An orbital shaker set at 30° C. and 175 rpm was used for incubation. Bioluminescence was then measured over a period of time. In order to evaluate the effect of saliva matrix, saliva samples were also spiked with a particular concentration of AI-2 and then incubated with the BB170 strain. For comparison purposes, the AI-2 concentration used for spiking was also incubated with the sensor strain. Calibration curves using standard AI-2 concentrations were obtained in each analytical run (FIG. 14).

Example 1

Whole-Cell Sensing Systems for Detecting AHLs

Figure 2B:
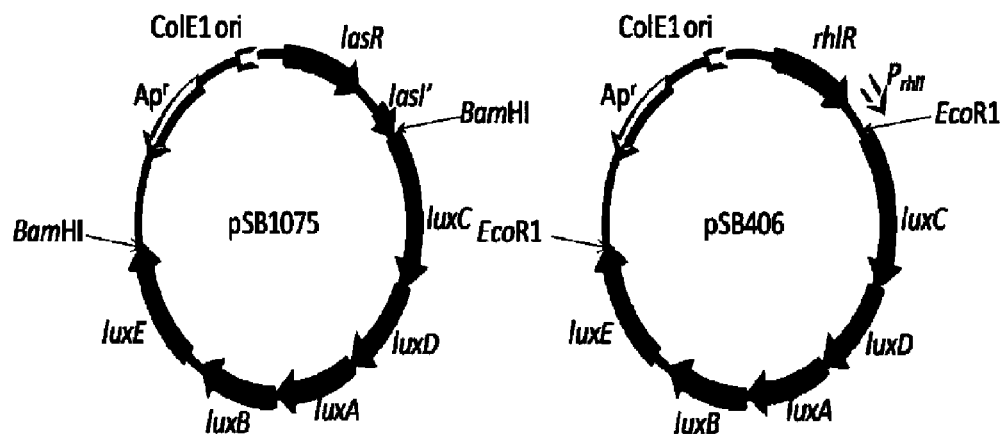

Two different whole-cell sensing systems were used, harboring either the pSB406 or pSB1075 plasmid, which are based on *P. aeruginosa* quorum sensing regulatory systems. [18] The plasmids pSB406 and pSB 1075 incorporate the genes rhlR and lasR, respectively, and the reporter gene cassette luxCDABE under transcriptional control of the promoters of the genes rhlI and lasI ($P_{rhlI}$ and $P_{lasI}$) respectively. Since the rhlI and lasI genes code for the synthases for the AHLs, they are not cloned into plasmids used for sensing. When AHLs are present in the environment of the sensing bacterial cells, they bind to the regulatory proteins RhlR and LasR. Subsequently, the regulatory protein-AHL complex binds to the corresponding promoter and activates gene transcription (see, e.g., FIG. 2A for a schematic representation of AHL-dependent regulation of quorum sensing in LuxR/LuxI-type systems, and FIG. 2B for a schematic representation of plasmids pSB1075 and pSB406). As a result, the luxCDABE cassette is expressed and a bioluminescent signal is produced. Further, the bioluminescence signal produced is directly proportional to the amount of the target AHL molecule present.

Example 2

Whole-Cell Sensing System for Detecting AI-2

*Vibrio harveyi* bioluminescent strain BB170 was used for the detection of AI-2 and was modified from the wild type *V. harveyi* so that it induces lux expression exclusively in response to AI-2. [23] AI-2 is detected by BB170 when it binds to the periplasmic protein LuxP. [24] AI-2 bound LuxP then activates inner membrane protein LuxQ. LuxQ is a hybrid two component kinase system, which includes periplasmic sensor domain, cytoplasmic histidine domain and response regulatory domains. At low cell density LuxQ acts as a kinase while at high cell density LuxQ acts as a phosphatase. As a kinase, it phosphorylates histidine residues in its histidine domain which in turn evokes a series of phophorylation steps leading to phosphorylation of phosphotransferase protein LuxU. LuxU transfers a phosphate group to LuxO which is a response regulator. Without wishing to be bound by any particular theory, it is thought that phosphorylated LuxO along with $\sigma^{54}$ activates expression of an unknown repressor X which represses the transcriptional activator LuxR. At high cell density, LuxQ changes from kinase to phosphatase by the action of AI-2 bound LuxP. As a phosphatase, LuxQ reverses the flow of the phosphoryl group from LuxO to LuxU to LuxQ. The dephosphorylated form of LuxO is inactive and repressor X is not expressed. LuxR is not repressed and thus binds the luxCDABE promoter, activating transcription of luciferase resulting in the production of light. BB170 also has a luxS gene producing its own AI-2 once it reaches high density. As such, the present assays were carried out using a BB170 culture of optimum density when inherent AI-2 production is at a minimum and AI-2 sensing system is active enough to respond to AI-2 present in the environment.

Example 3

Characterization of Whole-Cell Sensing Systems for Detecting AHLs

Figure 3:
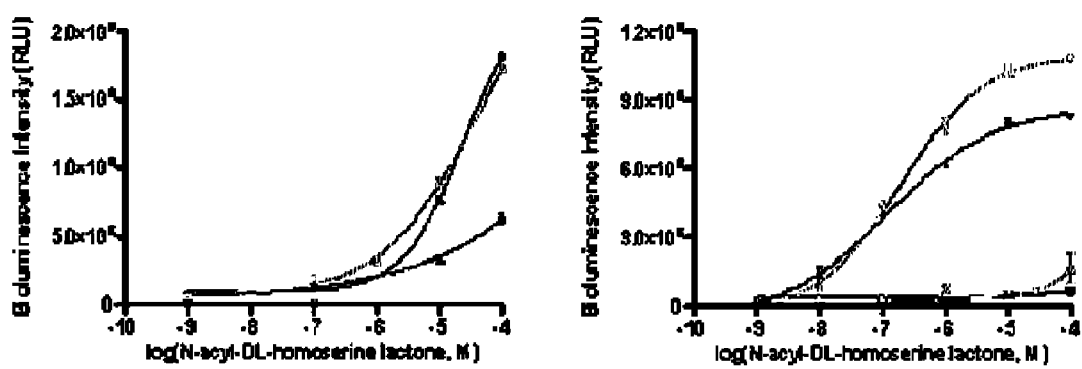
FIG. 3 includes calibration curves for exemplary cell sensing systems employing plasmid pSB406 (left panel) and pSB 1075 (right panel), where bacterial cells were incubated with different N-acyl-DL-homoserine lactones, namely, N-hexanoyl-DL-homoserine lactone (upward-pointing triangle), N-butyryl-DL-homoserine lactone (square), N-octanoyl-DL-homoserine lactone (circle), N-dodecanoyl-DL-homoserine lactone (diamond), and N-tetradecanoyl-DL-homoserine lactone (downward-pointing triangle), and where the signals have been corrected with respect to a blank, and where data shown are the average±one standard deviation.

Characterization of the whole-cell biosensing systems for the detection of AHLs was performed by incubating the bacterial cells with standard N-acyl homoserine lactone compounds with acyl side chains of different lengths. It has been reported that variations in length and substitutions in acyl side chains have significant effects on the binding/transcriptional activity of LuxR homologues, with the natural ligand generally being the most effective agonist. [19] In the experiments described herein, an increase in bioluminescence intensity was observed with increasing concentrations of the AHL compounds used. The molecules C4-HSL and C6-HSL, at the highest concentration tested ($1\times10^{-4}$ M), induced the maximum response in the biosensing system employing plasmid pSB406 (FIG. 3, left panel). Both compounds could be detected at concentrations as low as $1\times10^{-9}$ M, with a dynamic range of 4 orders of magnitude. The limit of detection was defined as the analyte concentration that produced a signal equal to or higher than the average signal produced by the blank plus three standard deviations. AHLs with longer acyl side chains were also able to activate the RhlRI regulatory system, although they did not induce the maximum response of the sensor and exhibited higher limits of detection as compared to C4-HSL and C6-HSL (Table 1).

TABLE 1

Analytical characteristics of the whole cell sensing system harboring the plasmid pSB406.

| AHL | Signal Intensity at $1 \times 10^{-4}$ M ($\times10^5$, RLU) | Limit of Detection (M) | Dynamic Range (M) |
|---|---|---|---|
| C4-HSL  | 19.99 ± 0.00 | $1 \times 10^{-9}$ | $1 \times 10^{-9}$-$1 \times 10^{-4}$ |
| C6-HSL  | 19.64 ± 0.25 | $1 \times 10^{-9}$ | $1 \times 10^{-9}$-$1 \times 10^{-4}$ |
| C8-HSL  | 6.87 ± 0.23  | $1 \times 10^{-9}$ | $1 \times 10^{-9}$-$1 \times 10^{-4}$ |
| C12-HSL | 8.40 ± 0.55  | $1 \times 10^{-8}$ | $1 \times 10^{-8}$-$1 \times 10^{-5}$ |
| C14-HSL | 4.22 ± 0.22  | $>1 \times 10^{-5}$ | — |

Data shown for signal intensity is the average ± one standard deviation.
The limit of detection was defined as the analyte concentration that produced a signal equal to or higher than the average signal produced by the blank plus three standard deviations.

The molecule C14-HSL, at the highest concentration tested ($1\times10^{-4}$ M), induced the maximum response in the whole-cell sensor bearing the plasmid pSB1075 (FIG. 3, right panel). The limit of detection was $1\times10^{-9}$ M for C14-HSL, as well as C12-HSL. Compounds with shorter acyl side chains either induced a response only at high concentrations or did not induce any response (Table 2).

TABLE 2

Analytical characteristics of the whole cell sensing system harboring the plasmid pSB1075.

| AHL | Signal Intensity at $1 \times 10^{-4}$ M ($\times10^5$, RLU) | Limit of Detection (M) | Dynamic Range (M) |
|---|---|---|---|
| C4-HSL  | 1.87 ± 0.06  | $1 \times 10^{-7}$ | $1 \times 10^{-7}$-$1 \times 10^{-4}$ |
| C6-HSL  | 2.53 ± 1.15  | $>1 \times 10^{-4}$ | — |
| C8-HSL  | 7.94 ± 0.70  | $1 \times 10^{-5}$ | $1 \times 10^{-5}$-$1 \times 10^{-4}$ |
| C12-HSL | 8.99 ± 0.17  | $1 \times 10^{-9}$ | $1 \times 10^{-9}$-$1 \times 10^{-5}$ |
| C14-HSL | 11.74 ± 0.09 | $1 \times 10^{-9}$ | $1 \times 10^{-9}$-$1 \times 10^{-4}$ |

Data shown for signal intensity is the average ± one standard deviation (n = 3).
The limit of detection was defined as the analyte concentration that produced a signal equal to or higher than the average signal produced by the blank plus three standard deviations.

These results are in agreement with those from other studies, which showed that long-chain AHLs induced the RhlRI regulatory system to a lesser extent than the LasRI regulatory system, while short-chain ARLs exhibited opposite behavior. [18] Both whole-cell sensing systems proved to be precise and reproducible, with intra- and interassay coefficients of variation less than 7%. Improved analytical performance was observed when the sensing cells were allowed to grow until the bacterial suspension reached an optical density of 0.45-0.50 at 600 nm. Substantially higher cell density values, which are accompanied by an increase in pH due to cell metabolism, were avoided because high pH values can lead to opening of the AHL lactone ring. [20]

These results were obtained using racemic mixtures of AHL compounds, rather than L-isomers. Although the AHLs present in nature are in the form of L-isomers, racemic mixtures proved to be representative of the single L-isomer activity. To confirm this, an exemplary whole-cell sensing system containing the plasmid pSB406 was incubated with either the L-isomer or DL-racemic mixture of 3-oxo-C6-HSL. The dose-response curves obtained showed no significant differences in the limit of detection, dynamic range, and maximum signal intensity at the highest analyte concentration.

The plasmids used in these studies have been constructed by taking advantage of the RhlI/RhlR and LasI/LasR quorum sensing systems of the Gram-negative bacterium *P. aeruginosa*. N-Butanoyl-L-homoserine lactone and N-(3-oxododecanoyl)-L-homoserine lactone are known to be the respective cognate activator molecules, i.e., the natural ligands that *P. aeruginosa* synthesize and sense, and to which *P. aeruginosa* respond. [1] The ability of the present cell sensing systems to respond to AHLs other than the cognate compound corresponding to the regulatory system broadens the applicability of these whole-cell sensing systems and renders them viable tools for the study of a wide range of bacteria-related conditions, which can involve a variety of microorganisms that use different AHLs as autoinducers in their quorum sensing regulatory systems.

Example 4

Analysis of Biological Samples for AHLs

Since the detection of AHLs in biological samples such as saliva and stool could be affected by components of the sample matrix, it was evaluated whether such an effect occurred with the whole-cell sensing systems by generating dose-response curves in pooled saliva and stool samples, respectively. The dose-response curves for the saliva and stool-based studies were obtained as described hereinabove in the Examples and were then compared with the reference calibration curves obtained in the absence of the biological matrix during the same analytical run.

Figure 4:
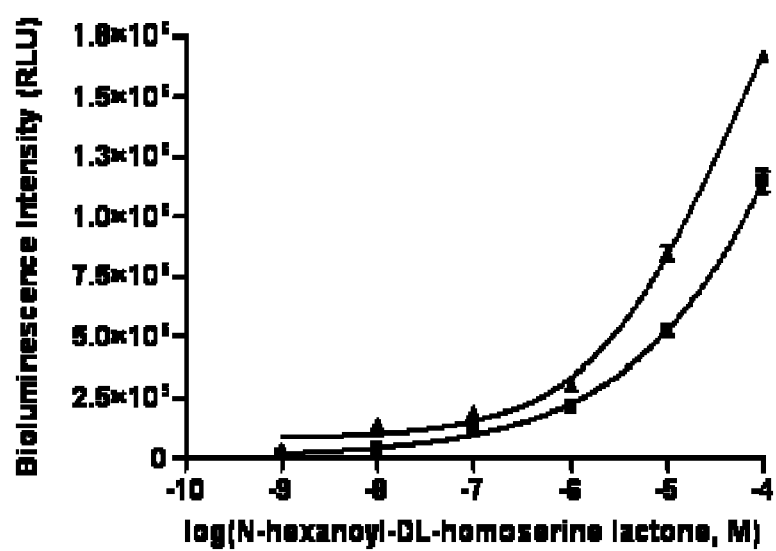
FIG. 4 includes an evaluation of saliva matrix effects using an exemplary biosensing system employing plasmid pSB406 and N-hexanoyl-DL-homoserine lactone as an analyte, where the dose-response curve is achieved by analyte standard addition to a pool of saliva samples from four healthy subjects (upward-pointing triangles) and the reference calibration curve (square) is obtained during the same analytical run, and where the signals have been corrected with respect to the blank, and where data shown are the average±one standard deviation.

Saliva contains viscous components that may render sample handling difficult and pipetting inaccurate and imprecise. Removal of viscous components and debris by centrifugation allowed for not only an improved sample quality but also eliminated sample matrix effects. Indeed, the dose-response curves generated in saliva exhibited slopes nearly identical to those corresponding to the reference calibration curves. For the stool-based study, the elimination of matrix effects was achieved by simple dilution of stool samples with deionized water, as shown by the nearly identical slopes observed for the dose-response curves obtained in the presence and absence of stool matrix. Overlapping curves were expected when analyte standard solutions were added to a sample originally containing no analyte. The dose-response curves in matrix showed higher signals when compared to the reference calibration curves, thus indicating the presence of AHLs in the pooled saliva and stool samples. FIG. 4 includes a representative example showing the response of the biosensing system employing plasmid pSB406 to N-hexanoyl homoserine lactone added to a pool of saliva samples. In the stool-based study, a dilution of 1:1600 (w/v) of stool sample in distilled, deionized water was chosen for all of the experiments since it allowed significant reduction in the matrix effect, when compared to lower dilution factors.

After assay optimization, the whole-cell sensing systems were employed to detect the presence of AHLs in saliva and stool samples collected from healthy and diseased subjects. Different levels of AHLs were detected in saliva of normal subjects and a subject affected by Crohn's disease, a chronic autoimmune inflammatory bowel disease that presents altered relative balance of the beneficial and detrimental commensal bacteria present in the gut (Table 3).

TABLE 3

Detection of AHLs in saliva samples from five healthy volunteers and one Crohn's patient using the sensing system harboring plasmid pSB406.

| Subjects | Signal Intensity (×10$^5$, RLU) | Percent Relative Standard Deviation (% RSD) |
|---|---|---|
| CD Patient | 0.54 ± 0.07 | 2.65 |
| Healthy Volunteers | | |
| 1 | 2.12 ± 0.06 | 1.50 |
| 2 | 0.89 ± 0.03 | 1.11 |
| 3 | 1.29 ± 0.05 | 1.31 |
| 4 | 1.35 ± 0.12 | 3.46 |
| 5 | 2.03 ± 0.09 | 2.13 |

The signals have been corrected with respect to the blank.
Data shown is the average ± one standard deviation (n = 3).

The levels varied significantly between normal subjects, while they were shown to be consistent for each individual over a period of time. Distinct levels of AHLs were detected also in stool samples of newborns admitted to the Neonatal Intensive Care Unit for various disorders (Table 4).

TABLE 4

Detection of AHLs in stool samples of infants in NICU (Newborn Intensive Care Unit) using the sensing system harboring plasmid pSB406.

| Subjects | Signal Intensity (×10$^5$, RLU) | Percent Relative Standard Deviation (% RSD) |
|---|---|---|
| 1 | 0.88 ± 0.05 | 2.44 |
| 2 | 0.92 ± 0.01 | 0.49 |
| 3 | 1.25 ± 0.01 | 0.59 |
| 4 | 1.19 ± 0.03 | 1.22 |

The signals have been corrected with respect to the blank.
Data shown is the average ± one standard deviation (n = 3).

Analysis of triplicates of individual saliva and stool samples showed that the present methods are also precise when applied to biological samples. These results were obtained on fresh samples that were processed and analyzed immediately after collection.

An assessment was further made of the stability of AHLs in saliva and stool samples depending upon storage conditions. In this assessment, it was demonstrated that saliva samples can be stored at least 1 day at room temperature, 4° C., and −20° C., while stool samples can be stored up to 3 days at −80° C., without observing significant differences in the amount of AHLs detected. Overall, the results achieved showed that the methods described herein can be successfully employed for the detection of AHLs in these samples.

Example 5

Analysis of Biological Samples for AI-2

Saliva samples were assayed for the presence of AI-2. Incubation of the samples with saliva with AI-2 sensing bacteria BB170 was performed in order to evaluate the effect of saliva matrix. Further, two saliva samples were spiked with a particular concentration of AI-2 and then incubated with the BB170 strain. Both saliva samples were spiked with AI-2 to obtain a final incubation concentration of $10^{-7}$ M AI-2. For comparison purposes, the AI-2 concentration used for spiking is also incubated with the sensor strain. Calibration curves using standard AI-2 concentrations were obtained in each analytical run (FIG. 14). Analysis of individual saliva samples showed that the present methods are precise when applied to biological samples and can be used for the detection of AI-2 molecules in saliva samples (Table 5).

TABLE 5

Analysis of saliva samples for AI-2 (S.S. = Spiked Saliva). Values shown are after 2.5 hours of incubation with the BB170 sensor strain.

| | Sample | Average Signal (RLU) | Std. Dev. | C.V. (%) |
|---|---|---|---|---|
| 1 | S.S. 1 | 160155 | 3862 | 2 |
| 2 | S.S. 2 | 527940 | 43995 | 8 |
| 3 | Saliva 1 | 90185 | 4354 | 5 |
| 4 | Saliva 2 | 403008 | 33383 | 8 |
| 5 | Blank | 228672 | 6789 | 3 |
| 6 | $10^{-7}$ M AI-2 | 324218 | 9773 | 3 |

Example 6

Detection of AHLs in Inflammatory Bowel Disease (IBD) Subjects

Figure 5:
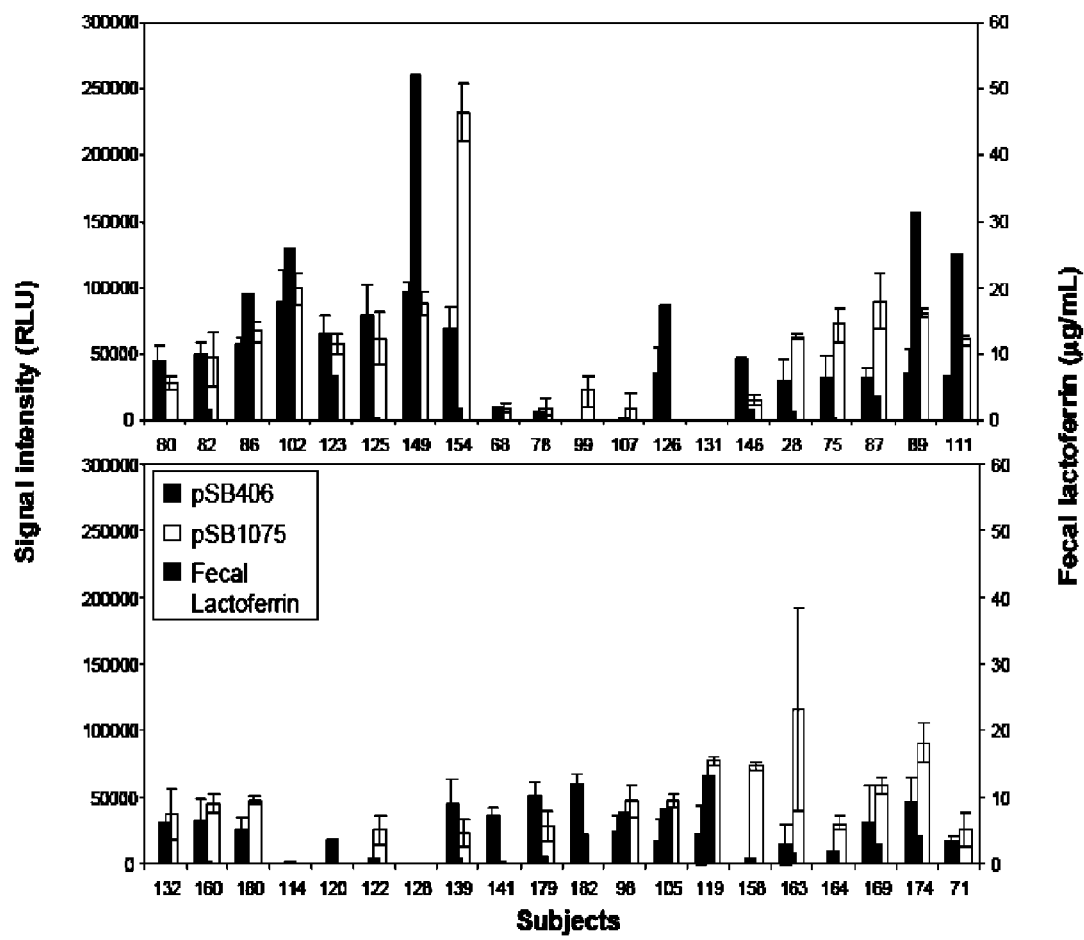
FIG. 5 is a graph depicting levels of short and long chain AHLs and fecal lactoferrin detected in bowel secretion samples from inflammatory bowel disease (IBD) subjects.

Bowel secretion samples were obtained from inflammatory bowel disease (IBD) subjects and healthy control subjects presenting to endoscopy for procedures associated with their IBD or for screening colonoscopy, respectively. A total of 40 bowel secretion samples were analyzed directly, without sample pretreatment, for the presence of AHLs. Two whole-cell sensing systems, based on bioluminescent genetically engineered bacterial cells bearing plasmid pSB406 or pSB1075, as described herein in the Examples, were used to allow for the detection of short and long chain AHLs, respectively. Twenty-eight out of 40 samples were shown to contain detectable levels of short chain AHLs, with concentrations ranging from $1 \times 10^{-8}$ to $1 \times 10^{-6}$ M. Thirty-three out of 40 samples were shown to contain detectable levels of long chain AHLs, with concentrations also ranging from $1 \times 10^{-8}$ to $1 \times 10^{-6}$ M. Samples were considered to be positive for AHLs when their signals were equal to or higher than the average signal of the blank plus 3 standard deviations. The bowel secretion samples were also analyzed for fecal lactoferrin, a molecule that is suggested to be a non-invasive, sensitive and specific biomarker representing intestinal inflammation in patients with IBD. For that, a commercially available immunoassay kit was employed. The AHL and fecal lactoferrin levels detected in bowel secretions are shown in FIG. 5.

Figure 6:
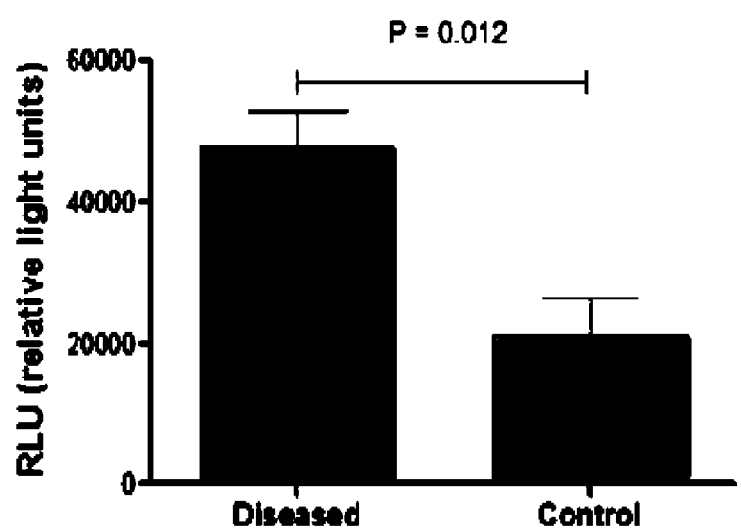
FIG. 6 is a graph showing a comparison between long chain AHL levels in diseased and control subjects.

A statistically significant difference in the levels of long chain AHLs was observed between IBD patients and controls (FIG. 6). An unpaired, two tailed t-test with Welch's correction was performed using GraphPad Prism version 5.00 (GraphPad Software, San Diego, Calif.).

Figure 7:
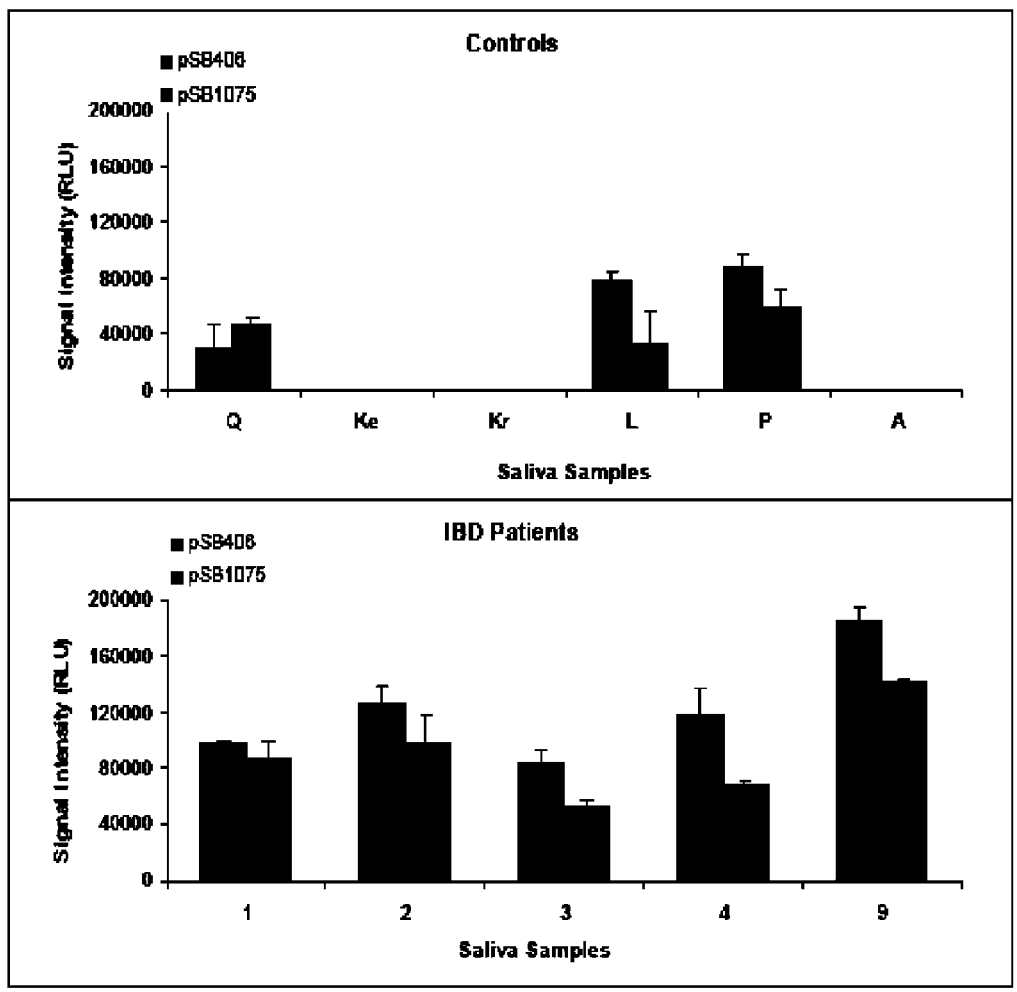
FIG. 7 contains graphs depicting levels of short and long chain AHLs detected in saliva samples from IBD subjects and control subjects.

Saliva samples were also collected from IBD patients and healthy controls. Short and long chain AHLs were detected in all of the patient samples analyzed, while both types of AHLs were detected in 3 out of 6 control samples (FIG. 7).

Example 7

Detection of AHLs in Newborn Infants

Figure 8:
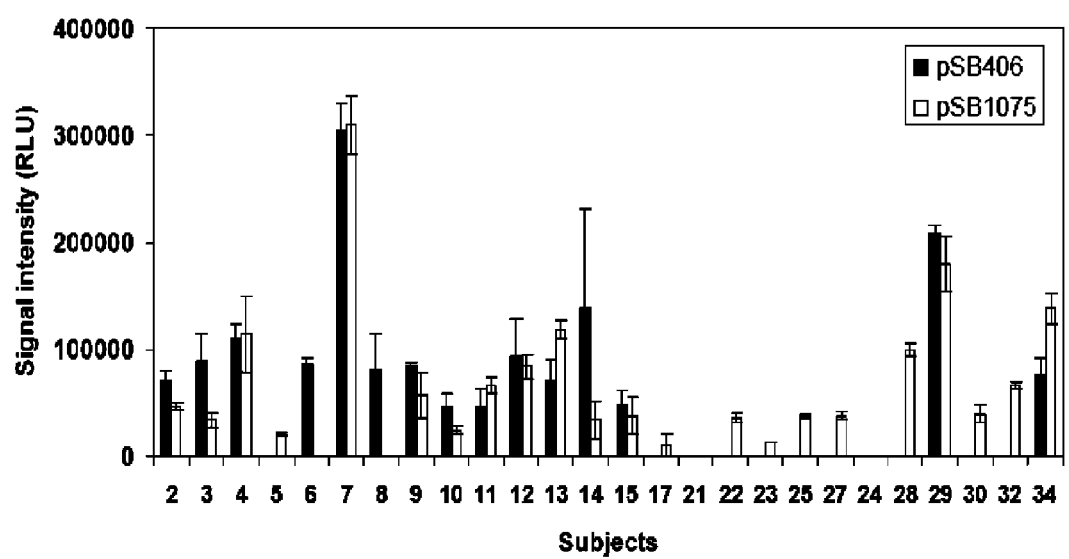
FIG. 8 is a graph depicting levels of short and long chain AHLs detected in stool samples from infants admitted to a Neonatal Intensive Care Unit (NICU).

AHLs were detected in stool samples from newborns admitted to a Neonatal Intensive Care Unit (NICU). It is appreciated that the NICU provides a diverse community of infants at an increased risk of inflammatory or infectious diseases. Bowel inflammation (necrotizing enterocolitis) and bacterial sepsis are typical examples of such illnesses affecting neonates. Thirty-four newborns were enrolled and monitored for a period of time, with stools collected once or twice a week. FIG. 8 reports the results obtained from the analysis of the samples collected from each infant upon admission/enrollment in the study. The presence of AHLs was detected in the stool of the majority of neonates, indicating the presence of gram-negative bacteria in their gut and pointing toward establishment of microflora early on in these neonates.

Example 8

Compact Disc Microfluidic Platform

Figure 10:
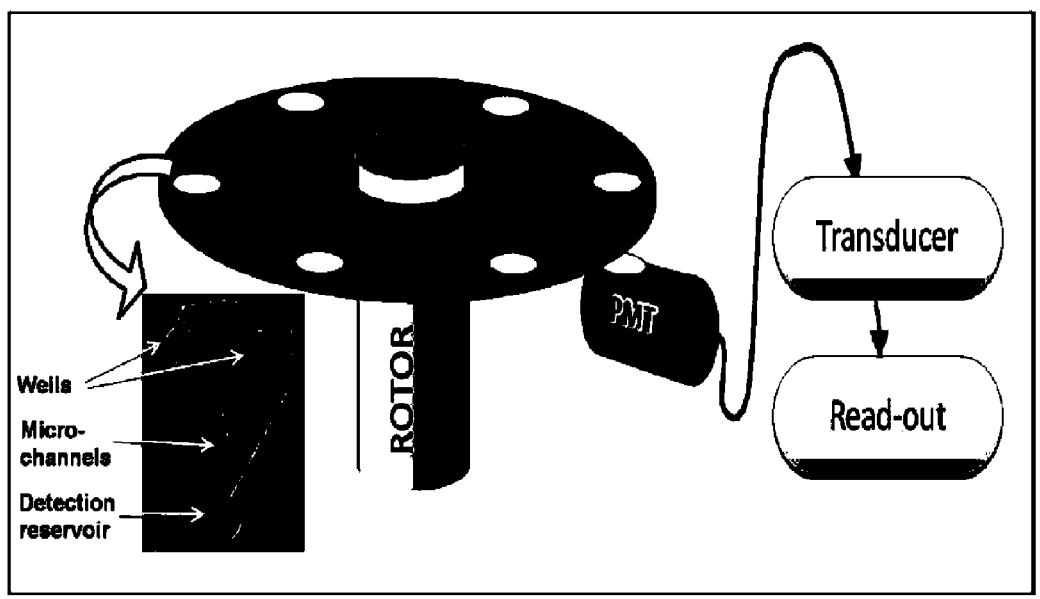
FIG. 10 is a schematic representation of an exemplary CD microfluidics platform attached to a rotor, where bioluminescent reactions in the microfluidic structures are detected by a photomultiplier tube (PMT) attached to a transducer that generates a readable signal.
Figure 11:
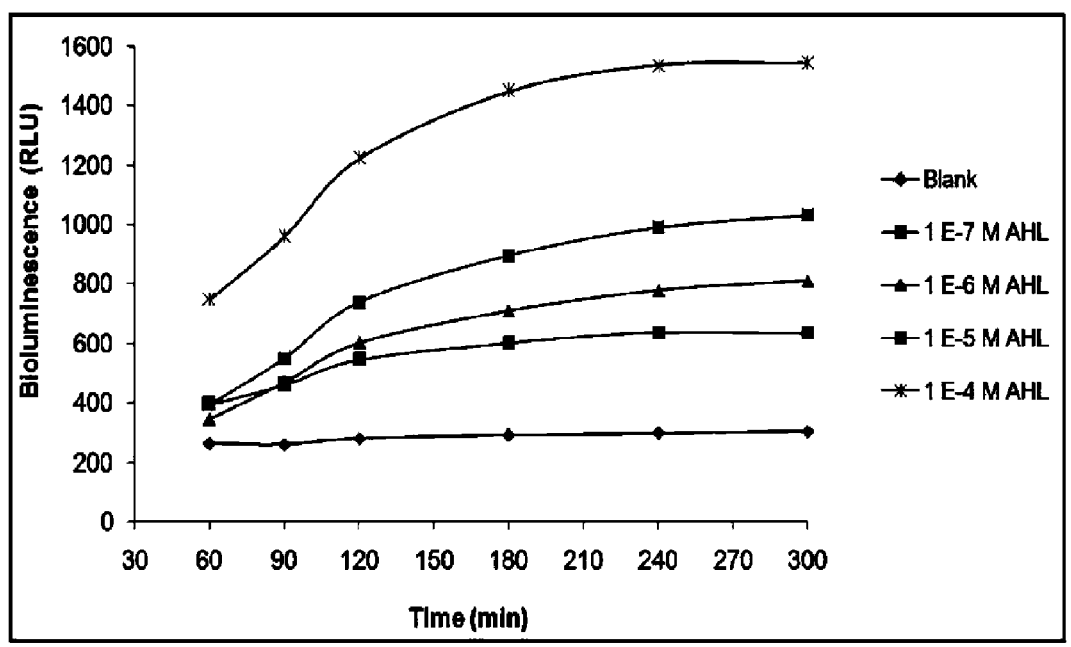
FIG. 11 is a graph depicting results of a time-course study using N-hexanoyl-DL-homoserine lactone in an exemplary CD microfluidics platform.
Figure 12:
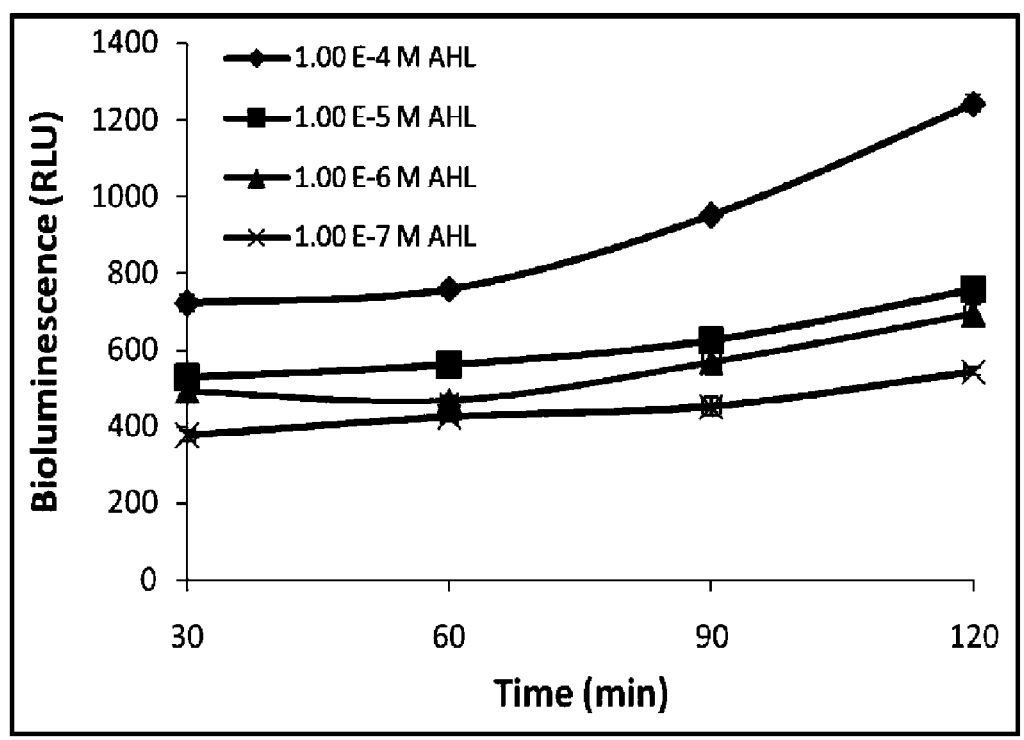
FIG. 12 is a graph depicting the reproducibility of an exemplary CD microfluidics platform for detecting quorum sensing molecules (QSMs).
Figure 13:
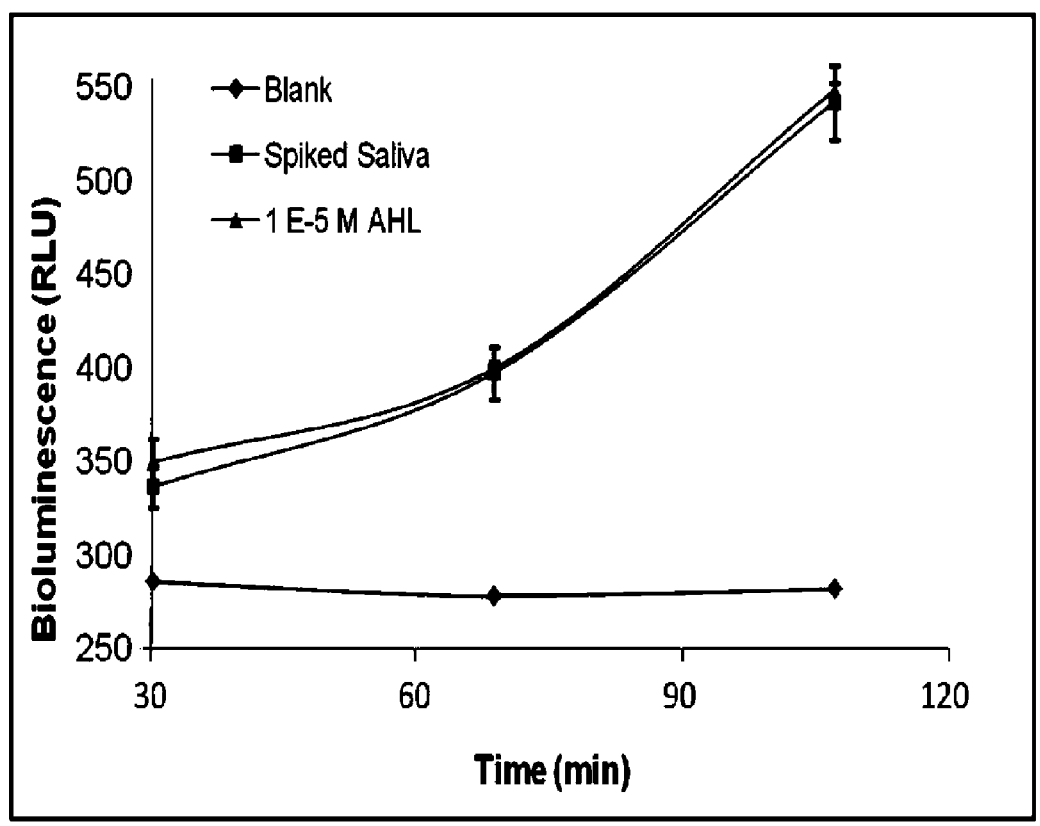
FIG. 13 is a graph depicting the ability of an exemplary CD microfluidics platform to detect QSMs in a biological sample.

To make the present methods, employing the whole-cell sensing systems, amenable to bedside and physician's office monitoring as well as home-based disease management, the bacterial cells harboring the plasmids pSB1075 and pSB406 were integrated into a compact disc microfluidics platform (FIG. 9A). In one experiment, an overnight culture of pSB406 sensing cells was grown at 37° C. and refreshed 1:15 the next day. A culture with an $O.D._{600\,nm}$ of 0.45-0.50 was then used in the platform. Serial dilutions of AHL were prepared ranging from $1\times10^{-4}$ M to $1\times10^{-7}$ M and 23 µL of a given concentration of AHL was added directly into the detection chamber of microfluidic structure (FIG. 9B). In one of the small wells, 7 µL of cell culture was added. Each structure was sealed carefully with clear tape. The disk was spun initially at a high velocity of 1200 rpm to insure simultaneous mixing of the solutions in each structure. The disk was then spun continuously at 800 rpm and readings were measured in a continuous manner by measuring the resulting bioluminescent signal from the bacteria in the detection chamber using a photomultiplier tube (PMT) attached to a transducer capable of generating "read-out" of the bioluminescent signal (FIG. 10). Miniaturization of the system resulted in an analytical performance that was similar to that observed previously for the whole-cell sensing systems not contained in a microfluidics platform, both in terms of detection limit (FIG. 11), i.e., $1\times10^{-7}$ M AHL, and reproducibility (FIG. 12). Further, the microfluidics platform was capable of detecting AHLs in a saliva sample obtained from a subject (FIG. 13).

Discussion of Examples 1-8

There is a need for understanding the mechanism involved in bacterial cell-to-cell communication as well as the role of this phenomenon in the onset and course of disease. This is important because it could provide useful insight in the pathogenesis of many bacteria-related disorders. Thus, there is a need for technologies capable of detecting bacterial communication in vivo, in real time, at low levels, and in biological samples. Although physical-chemical methods for the detection of AHLs and AI-2 are available, they are not quantitative and, therefore, appropriate for detailed investigations of quorum sensing mechanisms in biological matrixes, and for the design and evaluation of QS inhibitors as potential antimicrobial drugs. On the other hand, whole-cell biosensing systems are capable of providing information on the activity of the compounds present in a sample, and often detecting them directly, with no or minimal sample pretreatment. Additionally, they can easily, rapidly, and sensitively investigate large numbers of samples or compounds. Microorganisms are tolerant of suboptimal assay conditions and can be prepared in unlimited quantities relatively inexpensively. These characteristics make whole-cell sensing systems amenable to high-throughput screening, miniaturization, and automation. [13]

In the studies described herein in the Examples, methods were developed that are based on living whole-cell sensing systems. The methods were validated by employing them in the detection of AI-2 or in the detection of AHLs in saliva and stool samples from subjects with GI disorders. Saliva and stool analysis presents the advantage of enabling noninvasive collection of specimens. Further, the AI-2 and AHL concentrations in saliva or stool samples reflects systemic and gastrointestinal concentrations of an AI-2 and AHL, respectively. Indeed, fecal stream provides a mixture of gut flora, while the saliva concentrations of many molecules such as hormones and drugs have been demonstrated to reflect their blood concentrations. [15] Additionally, salivary levels of immunoglobulins of different classes, IgG, IgM, and IgA, have been reported to correlate with the status of subjects with GI disorders when compared with healthy controls. [16]

The methods, systems, and kits of the presently-disclosed subject matter can be employed in the diagnosis and management of various bacteria-related disorders. For instance, exemplary methods, systems, and kits of the presently-disclosed subject matter can be used to assess the correlation of QSMs in stool and saliva with diet, health indicators, and general health status of subjects with a variety of conditions associated with bacteria-related conditions. Demonstration of such correlation allows QSMs to be employed as biomarkers of these diseases.

Throughout this document, various references are mentioned. All such references are incorporated herein by reference, including the references set forth in the following list:

REFERENCES

1. Miller, M. B.; Bassler, B. L. *Annu. Rev. Microbiol.* 2001, 55, 165-199.
2. Taga, M. E.; Bassler, B. L. *Proc. Natl. Acad. Sci. U.S.A.* 2003, 100 Suppl 2, 14549-14554.
3. Hentzer, M.; Givskov, M. *J. Clin. Invest.* 2003, 112, 1300-1307.
4. Sartor, R. B. In *Kirsner's Inflammatory Bowel Diseases*, 6th ed.; Sartoc, R. B., Sandborn, W. J., Eds.; Elsevier: New York, 2004; pp 138-162.
5. Chandran, P.; Satthaporn, S.; Eremin, O.; Robins, A. *Surgeon* 2003, 1, 125.
6. Kjelleberg, S.; Molin, S. *Curr. Opin. Microbiol.* 2002, 5, 254-258.
7. Middleton, B.; Rodgers, H. C.; Camara, M.; Knox, A. J.; Williams, P.; Hardman, A. *FEMS Microbiol. Lett.* 2002, 207, 1-7.
8. Jarvas, K. G.; Giron, J. A.; Jerse, A. E.; McDaniel, T. K.; Donnenberg, M. S.; Kaper, J. B. *Proc. Natl. Acad. Sci. U.S.A.* 1995, 92, 7996-8000.
9. Chacon, O.; Bermudez, L. E.; Barletta, R. G. *Annu. Rev. Microbiol.* 2004, 58. 329-363.
10. Smith, R. S.; Iglewski, B. H. *J. Clin. Invest.* 2003, 112, 1460-1465.
11. Naylor, L. H. *Biochem. Pharmacol.* 1999, 58. 749-757.

12. Daunert, S.; Barrett, G.; Feliciano, J. S.; Shetty, R. S.; Shrestha, S.; Smith-Spencer, W. *Chem. Rev.* 2000, 100, 2705-2738.
13. Gu, M. B.; Mitchell, R. J.; Kim, B. C. *Adv. Biochem. Eng. Biotechnol.* 2004, 87, 269-305.
14. Feliciano, J.; Pasini, P.; Deo, S. K.; Daunert, S. In *Photoproteins in Bioanalysis*; Daunert, S., Deo, S. K., Eds.; Wiley-VCH: Weinheim, 2006; pp 131-154.
15. Kaufman, E.; Lamster, I. B. *Crit. Rev. Oral Biol. Med.* 2002, 13, 197-212.
16. Crama-Bohbouth, G.; Lems-van Kao, P.; Weterman, I. T.; Biermond, I.; Pena, A. S. *Dig. Dis. Sci.* 1984, 29, 1089-1092.
17. Van Dyk, T. K.; Rosson, R. *Methods Mol. Biol.* 1998, 102, 85-95.
18. Winson, M. K.; Swift, S.; Fish, L.; Throup, J. P., Jorgensen, F.; Chhabra, S. R.; Bycroft, B. W.; Williams, P.; Stewart, G. S. *FEMS Microbiol. Lett.* 1998, 163, 185-192.
19. Schaefer, A. L.; Hanzelka, B. L.; Eberhard, A.; Greenberg, E. P. *J. Bacteria* 1996, 178, 2897-2901.
20. Yates, E. A.; Philipp, B.; Buckley, C.; Atkinson, S.; Chhabra, S. R.; Sockett, R. E.; Goldner, M.; Dessaux, Y.; Camara, M.; Smith, H.; Williams, P. *Infect. Immun.* 2002, 70. 5635-5646.
21. Kumari, A.; Pasini, P.; Deo, S. K.; Flomenhoft, D.; Shashidhar, H.; Daunert, S. *Anal. Chem.* 2006, 78, 7603-7609.
22. Miller, S. T., et al. *Molecular Cell.* 2004, 15, 677-687.
23. Bassler, B. L.; Wright, M.; Silverman, M. R. *Mol. Microbiol.* 1994, 13(2), 273-286.
24. Mok, K. C.; Wingreen, N. S.; Bassler, B. L. *The EMBO J* 2003, 22(4), 870-881.

It will be understood that various details of the presently-disclosed subject matter can be changed without departing from the scope of the subject matter disclosed herein. Furthermore, the foregoing description is for the purpose of illustration only, and not for the purpose of limitation.

What is claimed is:

1. A method of diagnosing a bacteria-related condition of interest in a subject, comprising:
   providing a biological sample from a subject;
   determining an amount in the sample of at least one quorum sensing molecule (QSM), comprising one or more QSMs selected from the group consisting of
   an autoinducer-2 (AI-2), and
   at least one short-chain N-acyl homoserine lactone (AHL) and at least one long-chain N-acyl homoserine lactone; and
   comparing the amount of the at least one QSM in the sample, if present, to a control level of the at least one QSM, wherein the subject is diagnosed as having the bacteria-related condition of interest or a risk thereof if there is a measurable difference in the amount of the at least one QSM in the sample as compared to the control level, wherein the bacteria-related condition of interest is an inflammatory bowel disease (IBD).

2. The method of claim 1, wherein the subject is a human.
3. The method of claim 1, wherein the biological sample is a saliva sample.
4. The method of claim 1, wherein the biological sample is a stool sample.
5. The method of claim 1, wherein the at least one QSM comprises AI-2, and further comprises an N-acyl homoserine lactone (AHL).
6. The method of claim 5, wherein the AHL is selected from:
   N-butyryl homoserine lactone (C4-HSL),
   N-(3-oxo)-octanoyl homoserine lactone (3-oxo-C8-HSL),
   N-decanoyl homoserine lactone (C10-HSL),
   N-dodecanoyl homoserine lactone (C12-HSL),
   N-(3-oxo)-dodecanoyl homoserine lactone (3-oxo-C12-HSL),
   N-tetradecanoyl homoserine lactone (C14-HSL), and combinations thereof.

7. The method of claim 5, wherein the AHL is a short-chain AHL.
8. The method of claim 5, wherein the AHL is a long-chain AHL.
9. The method of claim 5, wherein the AHL is selected from:
   N-butyryl homoserine lactone (C4-HSL),
   N-hexanoyl homoserine lactone (C6-HSL),
   N-(3-oxo)-hexanoyl homoserine lactone (3-oxo-C6-HSL),
   N-octanoyl homoserine lactone (C8-HSL),
   N-(3-oxo)-octanoyl homoserine lactone (3-oxo-C8-HSL),
   N-decanoyl homoserine lactone (C10-HSL),
   N-dodecanoyl homoserine lactone (C12-HSL),
   N-(3-oxo)-dodecanoyl homoserine lactone (3-oxo-C12-HSL),
   N-tetradecanoyl homoserine lactone (C14-HSL), and combinations thereof.

10. The method of claim 1, wherein the IBD is selected from Crohn's disease (CD) and ulcerative colitis (UC).
11. The method of claim 1, wherein determining the amount in the sample of the at least one QSM comprises determining the amount in the sample of the at least one QSM using a cell sensing system.
12. The method of claim 1, further comprising selecting a treatment or modifying a treatment for the bacteria-related condition of interest based on the determined amount of the at least one QSM.
13. The method of claim 1, wherein the at least one QSM comprises an AI-2, and further comprises a short-chain AHL, and a long-chain AHL.
14. The method of claim 11, wherein the cell sensing system comprises:
   a bacterial cell;
   a regulatory protein within the bacterial cell for binding the at least one QSM; and
   a reporter molecule within the bacterial cell for detecting binding of the QSM to the regulatory protein, wherein the reporter molecule generates a detectable signal upon binding of the QSM to the regulatory protein.
15. The method of claim 14, wherein the cell sensing system further comprises a substrate supporting the bacterial cell and a signal reader for detecting the signal generated by the reporter molecule.
16. The method of claim 14, wherein the bacterial cell comprises a heterologous reporter gene cassette comprising a promoter operatively linked to a nucleotide sequence encoding the reporter molecule.
17. The method of claim 16, wherein the QSM-regulatory protein complex has binding affinity for the promoter, and wherein the regulatory peptide binds the promoter and activates expression of the reporter molecule, thereby generating a detectable signal.
18. The method of claim 16, wherein the reporter gene cassette is luxCDABE.
19. The method of claim 16, wherein the reporter gene cassette is luxCDABE, the promoter is $P_{rhlI}$, and the regulatory peptide is RhlR.
20. The method of claim 16, wherein the reporter gene cassette is luxCDABE, the promoter is $P_{lasI}$, and the regulatory peptide is LasR.

21. The method of claim 14, wherein the detectable signal is bioluminescence.

22. The method of claim 14, wherein an amount of the detectable signal correlates to a concentration of the QSM.

23. A method for determining whether to initiate or continue prophylaxis or treatment of a bacteria-related condition of interest in a subject, comprising:
(a) providing a series of biological samples over a time period from the subject;
(b) analyzing the series of biological samples to determine an amount in each of the biological samples of at least one QSM, comprising one or more QSMs selected from the group consisting of
an autoinducer-2 (AI-2), and
at least one short-chain N-acyl homoserine lactone (AHL) and at least one long-chain N-acyl homoserine lactone; and
(c) comparing any measurable change in the amounts of the at least one QSM in each of the biological samples to thereby determine whether to initiate or continue the prophylaxis or treatment of the bacteria-related condition of interest, wherein the bacteria-related condition of interest is an inflammatory bowel disease (IBD).

24. The method of claim 23, wherein the at least one QSM comprises an AI-2, a short-chain AHL, and a long-chain AHL.

25. The method of claim 23, wherein the subject is a human.

26. The method of claim 23, wherein the biological sample is a saliva sample.

27. The method of claim 23, wherein the biological sample is a stool sample.

28. The method of claim 23, wherein the at least one QSM comprises AI-2, and further comprises an N-acyl homoserine lactone (AHL).

29. The method of claim 28, wherein the AHL is selected from:
N-butyryl homoserine lactone (C4-HSL),
N-hexanoyl homoserine lactone (C6-HSL),
N-(3-oxo)-hexanoyl homoserine lactone (3-oxo-C6-HSL),
N-octanoyl homoserine lactone (C8-HSL),
N-(3-oxo)-octanoyl homoserine lactone (3-oxo-C8-HSL),
N-decanoyl homoserine lactone (C10-HSL),
N-dodecanoyl homoserine lactone (C12-HSL),
N-(3-oxo)-dodecanoyl homoserine lactone (3-oxo-C12-HSL),
N-tetradecanoyl homoserine lactone (C14-HSL), and
combinations thereof.

30. The method of claim 28, wherein the AHL is selected from:
N-butyryl homoserine lactone (C4-HSL),
N-(3-oxo)-octanoyl homoserine lactone (3-oxo-C8-HSL),
N-decanoyl homoserine lactone (C10-HSL),
N-dodecanoyl homoserine lactone (C12-HSL),
N-(3-oxo)-dodecanoyl homoserine lactone (3-oxo-C12-HSL),
N-tetradecanoyl homoserine lactone (C14-HSL), and
combinations thereof.

31. The method of claim 28, wherein the AHL is a short-chain AHL.

32. The method of claim 28, wherein the AHL is a long-chain AHL.

33. The method of claim 23, wherein the IBD is selected from Crohn's disease (CD) and ulcerative colitis (UC).

34. The method of claim 23, wherein determining the amount of the at least one QSM in each of the biological samples comprises determining the amount in the sample of the at least one QSM using a cell sensing system.

35. The method of claim 34, wherein the cell sensing system comprises:
a bacterial cell;
a regulatory protein within the bacterial cell for binding the at least one QSM; and
a reporter molecule within the bacterial cell for detecting binding of the QSM to the regulatory protein, wherein the reporter molecule generates a detectable signal upon binding of the QSM to the regulatory protein.

36. The method of claim 35, wherein the detectable signal is bioluminescence.

37. The method of claim 35, wherein an amount of the detectable signal correlates to a concentration of the QSM.

38. The method of claim 35, wherein the cell sensing system further comprises a substrate supporting the bacterial cell and a signal reader for detecting the signal generated by the reporter molecule.

39. The method of claim 35, wherein the bacterial cell comprises a heterologous reporter gene cassette comprising a promoter operatively linked to a nucleotide sequence encoding the reporter molecule.

40. The method of claim 39, wherein the QSM-regulatory protein complex has binding affinity for the promoter, and wherein the regulatory peptide binds the promoter and activates expression of the reporter molecule, thereby generating a detectable signal.

41. The method of claim 39, wherein the reporter gene cassette is luxCDABE.

42. The method of claim 39, wherein the reporter gene cassette is luxCDABE, the promoter is $P_{rhlI}$, and the regulatory peptide is RhlR.

43. The method of claim 39, wherein the reporter gene cassette is luxCDABE, the promoter is $P_{lasI}$, and the regulatory peptide is LasR.

* * * * *